US012653430B2

(12) United States Patent
Yang et al.

(10) Patent No.: US 12,653,430 B2
(45) Date of Patent: Jun. 16, 2026

(54) INTERFERENCE REJECTION MEMBRANES COMPRISING CROSSLINKED POLY (VINYL ALCOHOL) MATRICES FOR IMPLANTABLE GLUCOSE SENSORS

(71) Applicant: Medtronic MiniMed, Inc., Northridge, CA (US)

(72) Inventors: Qingling Yang, Northridge, CA (US); Robert C. Mucic, Glendale, CA (US); Rajiv Shah, Rancho Palos Verdes, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 721 days.

(21) Appl. No.: 17/515,098

(22) Filed: Oct. 29, 2021

(65) Prior Publication Data

US 2022/0047193 A1 Feb. 17, 2022

Related U.S. Application Data

(62) Division of application No. 15/140,129, filed on Apr. 27, 2016, now abandoned.

(51) Int. Cl.
A61B 5/1486 (2006.01)
A61B 5/145 (2006.01)
(Continued)

(52) U.S. Cl.
CPC ...... A61B 5/14865 (2013.01); A61B 5/14532 (2013.01); C12Q 1/006 (2013.01); G01N 27/403 (2013.01); A61B 2562/125 (2013.01)

(58) Field of Classification Search
CPC ............ C12Q 1/006; C12Q 1/00; C12Q 1/02; C12Q 1/34; C12Q 1/54; A61B 5/14532;
(Continued)

(56) References Cited

U.S. PATENT DOCUMENTS

| 4,755,173 | A | 7/1988 | Konopka et al. |
| 5,391,250 | A | 2/1995 | Cheney, II et al. |

(Continued)

FOREIGN PATENT DOCUMENTS

| JP | H4-132949 | 5/1992 |
| JP | 2004-512914 | 4/2004 |

(Continued)

OTHER PUBLICATIONS

Burshe et al., Separation and Purification Technology, 1997, 145-156 (Year: 1997).

(Continued)

Primary Examiner — Gurpreet Kaur
(74) Attorney, Agent, or Firm — GATES & COOPER LLP

(57) ABSTRACT

Embodiments of the invention provide amperometric analyte sensors having optimized elements such as interference rejection membranes as well as methods for making and using such sensors. The amperometric analyte sensor apparatus comprises: a base layer; a conductive layer disposed on the base layer and comprising a working electrode; an interference rejection membrane disposed on an electroactive surface of the working electrode, wherein the interference rejection membrane comprises poly(vinyl alcohol) (PVA) polymers crosslinked by an acid crosslinker, wherein the crosslinker is a dicarboxylic acid type monomer or a polymer comprising a carboxylic acid group; and an analyte sensing layer. While embodiments of the innovation can be used in a variety of contexts, typical embodiments of the invention include glucose sensors used in the management of diabetes.

18 Claims, 17 Drawing Sheets

Crosslinking chemistry of IRM membranes dialdehyde content monomers

PVA dicarboxylic acid content monomers crosslinked PVA

(51) Int. Cl.
  *C12Q 1/00*     (2006.01)
  *G01N 27/403*     (2006.01)

(58) Field of Classification Search
  CPC .......... A61B 5/14865; A61B 5/150274; A61B
        5/00; A61B 5/0022; A61B 5/7495; A61B
        5/150358; A61B 2562/125; G01N 27/327;
        G01N 27/3272; G01N 27/40; G01N
        27/48; G01N 27/26
  See application file for complete search history.

(56)            References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,275,717 B1 | 8/2001 | Gross et al. |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 2002/0127376 A1 | 9/2002 | Hutter et al. |
| 2004/0157131 A1 | 8/2004 | Fan et al. |
| 2005/0272989 A1 | 12/2005 | Shah et al. |
| 2007/0100222 A1 | 5/2007 | Mastrototaro et al. |
| 2007/0123819 A1 | 5/2007 | Mernoe et al. |
| 2007/0129697 A1 | 6/2007 | Soerens et al. |
| 2007/0244379 A1 | 10/2007 | Boock et al. |
| 2010/0025238 A1 | 2/2010 | Gottlieb et al. |
| 2010/0044316 A1 | 2/2010 | Childs et al. |
| 2010/0121169 A1 | 5/2010 | Petisce et al. |
| 2010/0160861 A1 | 6/2010 | Causey, III et al. |
| 2010/0163431 A1 | 7/2010 | Laitenberger et al. |
| 2011/0082356 A1 | 4/2011 | Yang et al. |
| 2013/0192987 A1 | 8/2013 | Watanabe et al. |

FOREIGN PATENT DOCUMENTS

| | | |
|---|---|---|
| JP | 2007-511737 | 5/2007 |
| JP | 2008-501415 | 1/2008 |
| JP | 2010-524554 | 7/2010 |
| WO | 9838906 | 3/1998 |
| WO | 2004060297 | 7/2004 |
| WO | 2005012873 | 2/2005 |

OTHER PUBLICATIONS

Sigma Aldrich product sheet.
Zhu etal. (Biosensor and Bioelectronics, 2013, 49, 210-215 (Year: 2013).
Japanese Office Action (with English translation) dated Jun. 3, 2014 for Japanese Patent Application No. 2012-532366.
International Search Report mailed Mar. 28, 2011, International application No. PCT/US2010/051177, International filing date Oct. 1, 2010.

Membrane Placement and Structure

110

112

114

120

104

Poly(vinyl alcohol)

Sulfosuccinic acid

Possible reaction mechanisms of PVA and SSA

FIG. 4

BTS and SITS Results based E2 substrate with M1 IRM formulation in vitro performance THICKER 2x GLM E2 substrate with M1 IRM formulation in vivo performance on dog

Poly(acrylic acid-co-maleic acid)

Poly(methyl vinyl ether-alt-maleic acid)

(PVA)

+

(Fumaric acid, FA )

Crosslinking
—————————→
150 °C (FA-crosslinked PVA)

INTERFERENCE REJECTION MEMBRANES COMPRISING CROSSLINKED POLY (VINYL ALCOHOL) MATRICES FOR IMPLANTABLE GLUCOSE SENSORS

CROSS REFERENCE TO RELATED APPLICATIONS

This application is a divisional application which claims the benefit under 35 U.S.C. § 120 and § 121 of U.S. patent application Ser. No. 15/140,129, filed Apr. 27, 2016, the contents of which are incorporated herein by reference. This application is related to U.S. patent application Ser. No. 11/633,254, U.S. patent application Ser. No. 12/184,046, U.S. patent application Ser. No. 12/345,354, and U.S. patent application Ser. No. 12/572,087, the contents of each of which are herein incorporated by reference.

BACKGROUND OF THE INVENTION

1. Field of the Invention

Analyte sensors (e.g. glucose sensors used in the management of diabetes) and methods and materials for making and using such sensors.

2. Description of Related Art

Analyte sensors such as biosensors include devices that use biological elements to convert a chemical analyte in a matrix into a detectable signal. There are many types of biosensors used for a wide variety of analytes. The most studied type of biosensor is the amperometric glucose sensor, which is crucial to the successful glucose level control for diabetes.

A typical glucose sensor works according to the following chemical reactions:

$$GLUCOSE + O_2 \xrightarrow{GLUCOSE\ OXIDASE} GLUCONIC\ ACID + H_2O_2 \qquad \text{Equation 1}$$

$$H_2O_2 \rightarrow O_2 + 2H^+ + 2e^- \qquad \text{Equation 2}$$

The glucose oxidase is used to catalyze the reaction between glucose and oxygen to yield gluconic acid and hydrogen peroxide (Equation 1). The $H_2O_2$ reacts electrochemically as shown in Equation 2, and the current can be measured by a potentiostat. These reactions, which occur in a variety of oxidoreductases known in the art, are used in a number of sensor designs.

One common problem with electrochemical sensors is that they can electrochemically react not only with the analyte to be measured (or by-product of the enzymatic reaction with the analyte), but can also react with other electroactive chemical species that are not intentionally being measured, which causes an increase in signal strength due to these "interfering species". Typically, such interfering species are compounds with an oxidation or reduction potential that overlaps with the analyte to be measured (or by-product of the enzymatic reaction with the analyte). For example, in a conventional amperometric glucose oxidase-based glucose sensor wherein the sensor measures hydrogen peroxide, interfering species such as acetaminophen, ascorbate, and urate are known to confound true analyte signals.

For this reason, methods and materials designed to address the difficulties caused by such interfering species are desirable.

Eliminating interference from small neutral molecules such as acetaminophen (Mw 150) is always very challenging, considering that its size is even smaller than glucose (Mw 180). Direct coating of a polymer thin film is normally unable to adequately eliminate this interference due to its insufficient density, even if a very high molecular weight polymer is used. In order to maintain sensor signals at a high level, the membrane structure is ideally extremely dense and thin.

Furthermore, appropriate hydrophilicity is also required when considering the start-up time of an implanted sensor and the subsequent stability of the sensor's electrical output (Isig). If the membrane is too hydrophobic or too thick, it may need longer time to become hydrated even though it may have good interference rejection capability. If the membrane is too hydrophilic, the membrane may keep swelling and the Isig may drift up as time goes by. Thus, an appropriate control membrane material composition and suitable thickness is the key to obtaining good overall sensor performance.

SUMMARY OF THE INVENTION

The present invention relates to methods and materials designed to improve sensor sensitivity and address the difficulties caused by interfering species. Embodiments of the invention include crosslinked polymeric membrane compositions that can be used, for example, as barriers for interfering species in analyte sensors and sensor systems such as amperometric glucose sensors that are commonly used in the management of diabetes. In particular, embodiments of the invention include IRMs (interference rejection membranes) based on various acid crosslinked poly(vinyl alcohol) (PVA) and functional PVA polymers. Sensors based on these structures have demonstrated high interference rejection, good oxygen effect character, extremely fast start-up, and satisfactory in vivo and in vitro performances in various illustrative experiments. Such embodiments provide significant commercial value to current implantable glucose sensor applications.

One embodiment of the invention is an amperometric analyte sensor apparatus comprising: a base layer; a conductive layer disposed on the base layer and comprising a working electrode; an interference rejection membrane disposed on an electroactive surface of the working electrode, wherein the interference rejection membrane comprises poly (vinyl alcohol) polymers crosslinked by an acid crosslinker, wherein the crosslinker is a dicarboxylic acid type monomer or a polymer comprising a carboxylic acid group; and an analyte sensing layer. In specific embodiments of this sensor, the interference rejection membrane comprises 5 wt % poly(vinyl alcohol) crosslinked with 10-20 wt % crosslinker. Typically, the poly(vinyl alcohol) polymer has a molecular weight (Mw) of at least 45K. In further instances, the degree of hydrolysis of the poly(vinyl alcohol) polymer is at least 98%.

In various embodiments of the invention, the crosslinker is selected from the group consisting of sulfosuccinic acid (SSA), maleic acid, citric acid, oxalic acid, fumaric acid, poly(acrylic acid), poly(acrylic acid-co-maleic acid) (PAM), succinic acid, malonic acid, and poly(methyl vinyl ether-alt-maleic acid). In one instance, the crosslinker is sulfosuccinic acid. In certain embodiments, the interference rejection membrane comprises 5-50 wt % sulfosuccinic acid (based on the polymer weight of PVA in solution). In one illustrative implementation, the interference rejection membrane comprises 5 wt % poly(vinyl alcohol) crosslinked with 10 wt % sulfosuccinic acid. In another instance, the cross-linker is poly(methyl vinyl ether-alt-maleic acid).

Typically, the interference rejection membrane inhibits the diffusion therethrough of compounds having a molecular weight greater than 140 Daltons (e.g. acetaminophen, uric acid, ascorbic acid and the like). In one such embodiment of the invention, the interference rejection membrane inhibits the diffusion of acetaminophen (molecular weight 151.17 Daltons) therethrough in a manner that decreases a signal in the analyte sensor apparatus that results from a concentration of acetaminophen by at least 50% as compared to a control analyte sensor apparatus lacking the interference rejection membrane. Typically, the interference rejection membrane has a thickness of 0.3-2 $\mu$m. In specific instances, the interference rejection membrane has a thickness from 0.4 to 0.8 $\mu$m or from 0.3-0.5 $\mu$m.

Certain analyte sensor embodiments of the invention can be implanted in vivo and typically comprise a plurality of functional layers disposed on one another, for example a base layer; a conductive layer disposed on the base layer and comprising a working electrode; an interference rejection membrane disposed on an electroactive surface of the working electrode, an analyte sensing layer coated directly on top of the interference rejection membrane and further comprising at least one of: a protein layer disposed on the analyte sensing layer; an analyte modulating layer disposed on the analyte sensing layer or the protein layer, wherein the analyte modulating layer comprises a composition that modulates the diffusion of an analyte diffusing through the analyte modulating layer; an adhesion promoting layer disposed on the analyte sensing layer, wherein the adhesion promoting layer promotes the adhesion between the analyte sensing layer and an analyte modulating layer; or a cover layer disposed on the analyte sensor apparatus, wherein the cover layer comprises an aperture positioned on the cover layer so as to facilitate an analyte present in vivo accessing and diffusing through an analyte modulating layer; and then accessing the analyte sensing layer. Typically, the analyte sensing layer comprises an oxidoreductase that generates hydrogen peroxide upon exposure to a substrate for the oxidoreductase, wherein the amount of hydrogen peroxide generated by the oxidoreductase is proportional to the amount of substrate exposed to the oxidoreductase.

Certain analyte sensor embodiments of the invention include a conductive layer that comprises a plurality of electrodes including the working electrode, a counter electrode and a reference electrode. Optionally, the conductive layer comprises a plurality of working electrodes, counter electrodes and reference electrodes grouped together as a unit and positionally distributed on the conductive layer in a repeating pattern of units. In some embodiments of the invention, the sensor is operatively coupled to: a sensor input capable of receiving a signal from the sensor that is based on a sensed physiological characteristic value in vivo; and a processor coupled to the sensor input, wherein the processor is capable of characterizing one or more signals received from the sensor. Optionally, a pulsed voltage is used to observe a signal from a working electrode of a sensor.

Another embodiment of the invention is a method of making a sensor apparatus for implantation within a mammal comprising the steps of: providing a base layer; forming a conductive layer on the base layer, wherein the conductive layer includes a working electrode; forming an interference rejection membrane on the working electrode, wherein the interference rejection membrane comprises poly(vinyl alcohol) polymers crosslinked with sulfosuccinic acid or poly (methyl vinyl ether-alt-maleic acid); forming an analyte sensing layer on the conductive layer, wherein the analyte sensing layer includes an oxidoreductase; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. Typically, the interference rejection membrane is between 0.3-2 $\mu$m thick and formed on the electrode by a spin coating process at 400-1200 rpm and cured at a temperature between 130° C.-150° C. In one specific instance, the interference rejection membrane is between 0.4-0.8 $\mu$m thick and formed on the electrode by a spin coating process at 400-500 rpm and cured at a temperature of 130° C.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE FIGURES

FIG. 4 provides a schematic of a possible reaction mechanism occurring during the crosslinking of poly(vinyl alcohol) (PVA) polymers with sulfosuccinic acid (SSA), in accordance with one or more embodiments of the invention.

Figure 11:
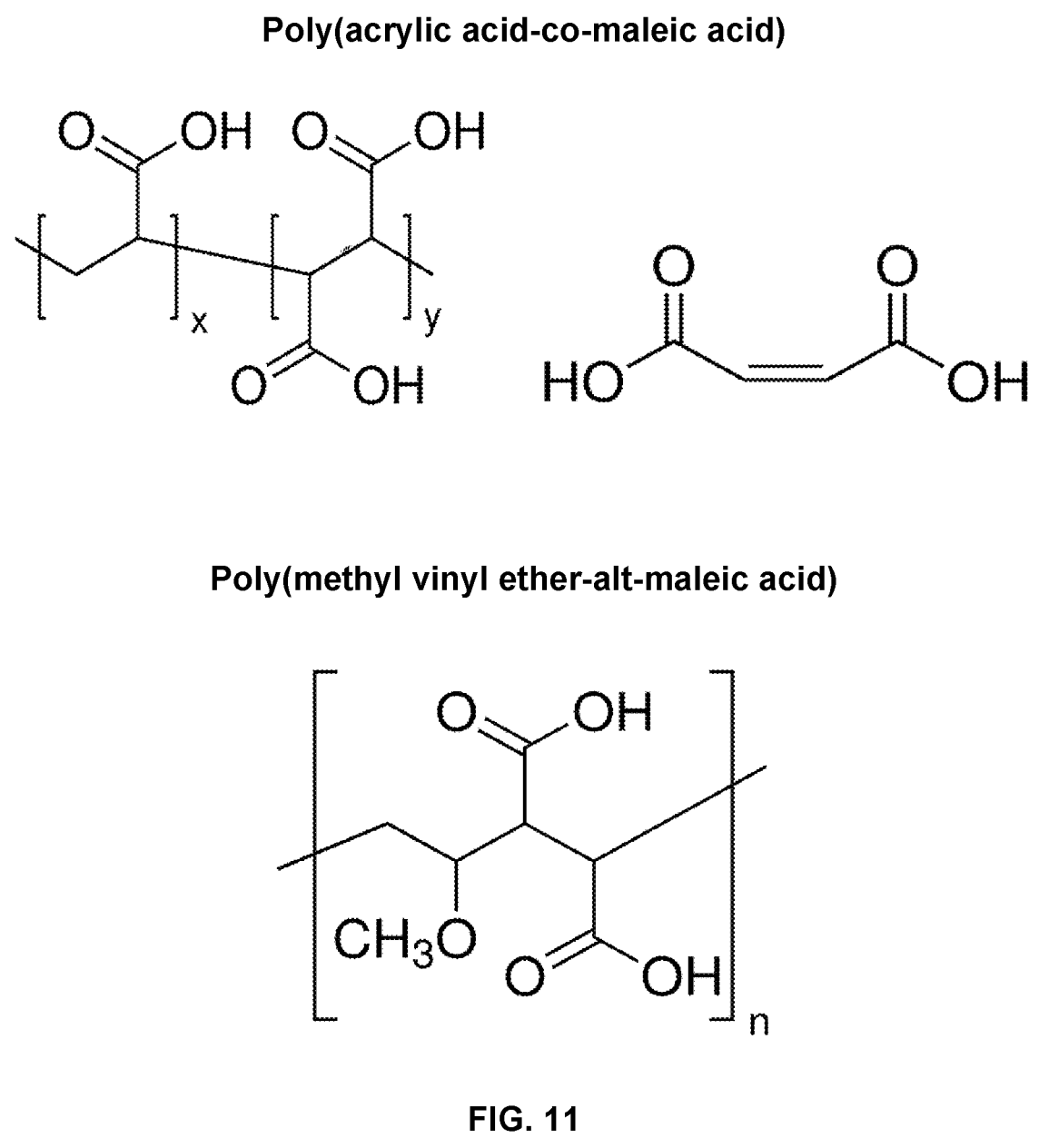

FIG. 11 provides illustrations of the molecular structures for poly(acrylic acid-co-maleic acid) and poly(methyl vinyl ether-alt-maleic acid).

Figure 12:
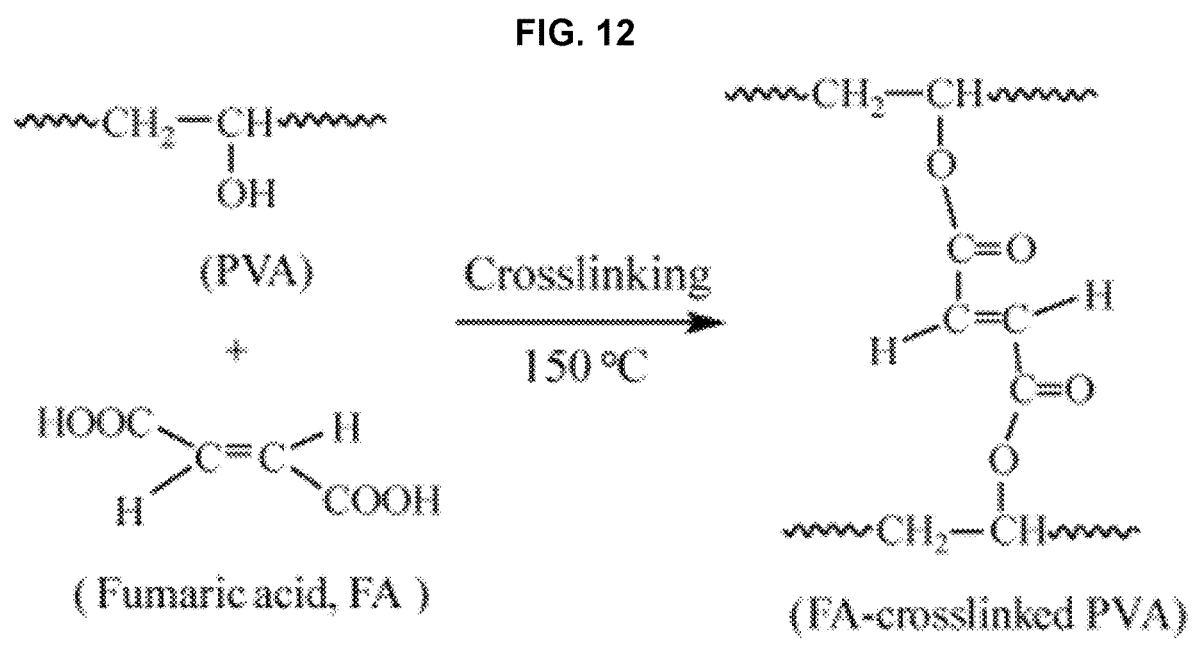

FIG. 12 provides an illustration of the crosslinking of poly(vinyl alcohol) (PVA) by fumaric acid (FA), in accordance with one or more embodiments of the invention.

DETAILED DESCRIPTION OF THE INVENTION

Figure 1:
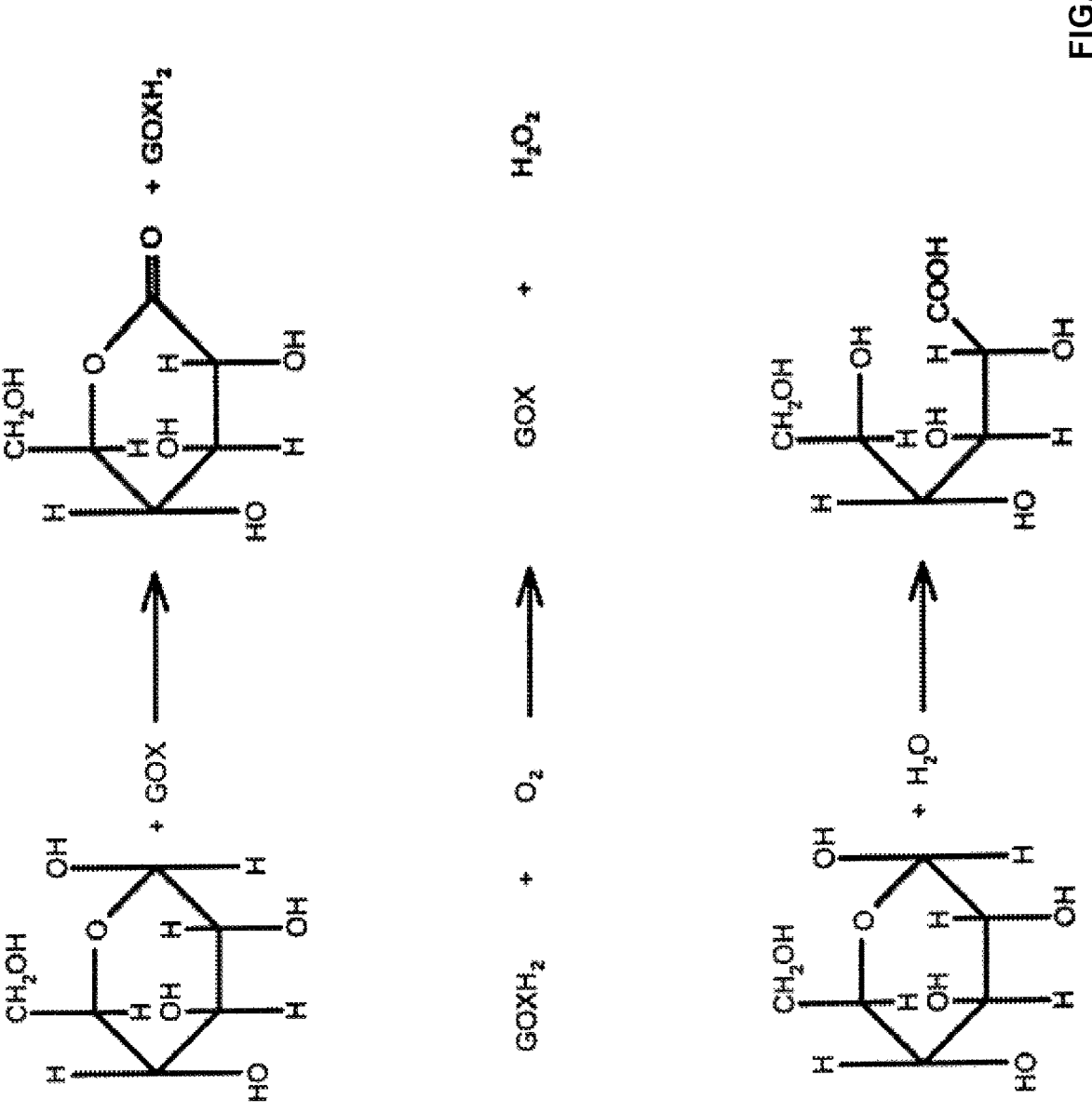
FIG. 1 provides a schematic of the well known reaction between glucose and glucose oxidase. As shown in a stepwise manner, this reaction involves glucose oxidase (GOx), glucose, and oxygen in water. In the reductive half of the reaction, two protons and electrons are transferred from $\beta$-D-glucose to the enzyme yielding d-gluconolactone. In the oxidative half of the reaction, the enzyme is oxidized by molecular oxygen yielding hydrogen peroxide. The d-gluconolactone then reacts with water to hydrolyze the lactone ring and produce gluconic acid. In certain electrochemical sensors of the invention, the hydrogen peroxide produced by this reaction is oxidized at the working electrode ($H_2O_2 \rightarrow 2H^+ + O_2 + 2e^-$).

Unless otherwise defined, all terms of art, notations, and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted. In addition, certain text from related art is reproduced herein to more clearly delineate the various embodiments of the invention. A number of terms are defined below.

All publications mentioned herein are expressly incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

It must be noted that as used herein and in the appended claims, the singular forms "a", "and", and "the" include plural referents unless the context clearly dictates otherwise. Thus, for example, reference to "an oxidoreductase" includes a plurality of such oxidoreductases and equivalents thereof known to those skilled in the art, and so forth. All numbers recited in the specification and associated claims that refer to values that can be numerically characterized with a value other than a whole number (e.g. the concentration of a compound in a solution) are understood to be modified by the term "about".

The term "oxidoreductase" is used according to its art accepted meaning, i.e. an enzyme that catalyzes the transfer of electrons from one molecule (the reductant, also called the hydrogen or electron donor) to another (the oxidant, also called the hydrogen or electron acceptor). Typical oxidoreductases include glucose oxidase and lactate oxidase. The term "carrier polypeptide" or "carrier protein" is used according to its art accepted meaning of an additive included to maintain the stability of a polypeptide, for example the ability of an oxidoreductase polypeptide to maintain certain qualitative features such as physical and chemical properties (e.g. an ability to oxidize glucose) of a composition comprising a polypeptide for a period of time. A typical carrier protein commonly used in the art is albumin.

The term "analyte" as used herein is a broad term and is used in its ordinary sense, including, without limitation, to refer to a substance or chemical constituent in a fluid such as a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to, lactate. Salts, sugars, proteins fats, vitamins and hormones naturally occurring in blood or interstitial fluids can constitute analytes in certain embodiments. The analyte can be naturally present in the biological fluid or endogenous; for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to insulin. The metabolic products of drugs and pharmaceutical compositions are also contemplated analytes.

The terms "interferents" and "interfering species/compounds" are used in their ordinary sense, including, but not limited to, effects and/or chemical species/compounds that interfere with the measurement of an analyte of interest in a sensor to produce a signal that does not accurately represent the analyte measurement. In one example of an electrochemical sensor, interfering species are compounds with an oxidation potential that overlaps with the analyte to be measured so as to produce spurious signals.

The term "sensor," as used herein, is a broad term and is used in its ordinary sense, including, without limitation, the portion or portions of an analyte-monitoring device that detects an analyte. In one embodiment, the sensor includes an electrochemical cell that has a working electrode, a reference electrode, and optionally a counter electrode passing through and secured within the sensor body forming an electrochemically reactive surface at one location on the body, an electronic connection at another location on the body, and a membrane system affixed to the body and covering the electrochemically reactive surface. During general operation of the sensor, a biological sample (for example, blood or interstitial fluid), or a portion thereof, contacts (directly or after passage through one or more membranes or domains) an enzyme (for example, glucose oxidase); the reaction of the biological sample (or portion thereof) results in the formation of reaction products that allow a determination of the analyte level in the biological sample.

The terms "electrochemically reactive surface" and "electroactive surface" as used herein are broad terms and are used in their ordinary sense, including, without limitation, the surface of an electrode where an electrochemical reaction takes place. In one example, a working electrode (e.g. one comprised of platinum black) measures the hydrogen peroxide produced by the enzyme-catalyzed reaction of the analyte being detected by creating an electric current. For example, detection of glucose analyte utilizing glucose oxidase produces $H_2O_2$ as a by-product. The $H_2O_2$ reacts with the surface of the working electrode producing two protons ($2H^+$), two electrons ($2e^-$), and one molecule of oxygen ($O_2$) which produces the electronic current being detected. In the case of the counter electrode, a reducible species, for example, $O_2$ is reduced at the electrode surface in order to balance the current being generated by the working electrode.

The term "sensing region" as used herein is a broad term and is used in its ordinary sense, including, without limitation, the region of a monitoring device responsible for the detection of a particular analyte. In an illustrative embodiment, the sensing region can comprise a non-conductive body, a working electrode, a reference electrode, and a counter electrode passing through and secured within the body forming electrochemically reactive surfaces on the body and an electronic connective means at another location on the body, and a one or more layers covering the electrochemically reactive surface.

As discussed in detail below, embodiments of the invention relate to the use of an electrochemical sensor that exhibits a novel constellation of elements including an interference rejection membrane having a unique set of technically desirable material properties. The electrochemical sensors of the invention are designed to measure a concentration of an analyte of interest (e.g. glucose) or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples. The sensor embodiments disclosed herein can use any known method, including invasive, minimally invasive, and non-invasive sensing techniques, to provide an output signal indicative of the concentration of the analyte of interest. Typically, the sensor is of the type that senses a product or reactant of an enzymatic reaction between an analyte and an enzyme in the presence of oxygen as a measure of the analyte in vivo or in vitro. Such sensors typically comprise a membrane surrounding the enzyme through which an analyte migrates. The product is then measured using electrochemical methods and thus the output of an electrode system functions as a measure of the analyte. In some embodiments, the sensor can use an amperometric, coulometric, conductimetric, and/or potentiometric technique for measuring the analyte.

Embodiments of the invention disclosed herein provide sensors of the type used, for example, in subcutaneous or transcutaneous monitoring of blood glucose levels in a diabetic patient. A variety of implantable, electrochemical biosensors have been developed for the treatment of diabetes and other life-threatening diseases. Many existing sensor designs use some form of immobilized enzyme to achieve their bio-specificity. Embodiments of the invention described herein can be adapted and implemented with a wide variety of known electrochemical sensors, including for example, U.S. Patent Application No. 20050115832, U.S. Pat. Nos. 6,001,067, 6,702,857, 6,212,416, 6,119,028, 6,400,974, 6,595,919, 6,141,573, 6,122,536, 6,512,9395, 605,152, 4,431,004, 4,703,756, 6,514,718, 5,985,129, 5,390, 691, 5,391, 250, 5,482,473, 5,299,571, 5,568,806, 5,494, 562, 6,120,676, 6,542,765 as well as PCT International Publication Numbers WO 01/58348, WO 04/021877, WO 03/034902, WO 03/035117, WO 03/035891, WO 03/023388, WO 03/022128, WO 03/022352, WO 03/023708, WO 03/036255, WO03/036310 WO 08/042625, and WO 03/074107, and European Patent Application EP 1153571, the contents of each of which are incorporated herein by reference.

As discussed in detail below, embodiments of the invention disclosed herein provide sensor elements having enhanced material properties and/or architectural configurations and sensor systems (e.g. those comprising a sensor and associated electronic components such as a monitor, a processor and the like) constructed to include such elements. The disclosure further provides methods for making and using such sensors and/or architectural configurations. While some embodiments of the invention pertain to glucose and/or lactate sensors, a variety of the elements disclosed herein (e.g. interference rejection membranes) can be adapted for use with any one of the wide variety of sensors known in the art. The analyte sensor elements, architectures, and methods for making and using these elements that are disclosed herein can be used to establish a variety of layered sensor structures. Such sensors of the invention exhibit a surprising degree of flexibility and versatility, characteristics which allow a wide variety of sensor configurations to be designed to examine a wide variety of analyte species.

Specific aspects of embodiments of the invention are discussed in detail in the following sections.

I. Typical Elements, Configurations and Analyte Sensor Embodiments of the Invention A wide variety of sensors and sensor elements are known in the art including amperometric sensors used to detect and/or measure biological analytes such as glucose. Many glucose sensors are based on an oxygen (Clark-type) amperometric transducer (see, e.g. Yang et al., Electroanalysis 1997, 9, No. 16: 1252-1256; Clark et al., Ann. N.Y. Acad. Sci. 1962, 102, 29; Updike et al., Nature 1967, 214,986; and Wilkins et al., Med. Engin. Physics, 1996, 18, 273.3-51). A number of in vivo glucose sensors utilize hydrogen peroxide-based amperometric transducers because such transducers are relatively easy to fabricate and can readily be miniaturized using conventional technology. A problem associated with the use of hydrogen peroxide-based amperometric transducers, however, is signal interference due to electroactive substances present in the analyte environment. Current sensors in the art commonly lack selectivity against other electrochemically reactive substances such as acetaminophen and other drugs, which would lead to significant false signals if not eliminated. As discussed in detail below, these problems are addressed by the novel semipermeable membranes disclosed herein that modulate the transport properties of different compounds that can create a signal in the hydrogen peroxide-based amperometric transducing element (e.g. electrodes of various sizes, architectures and compositions). Consequently, these membranes can be used with any of a variety of $H_2O_2$-based transducers used in analyte sensors that are susceptible to interference from electroactive substances.

Figure 2A:
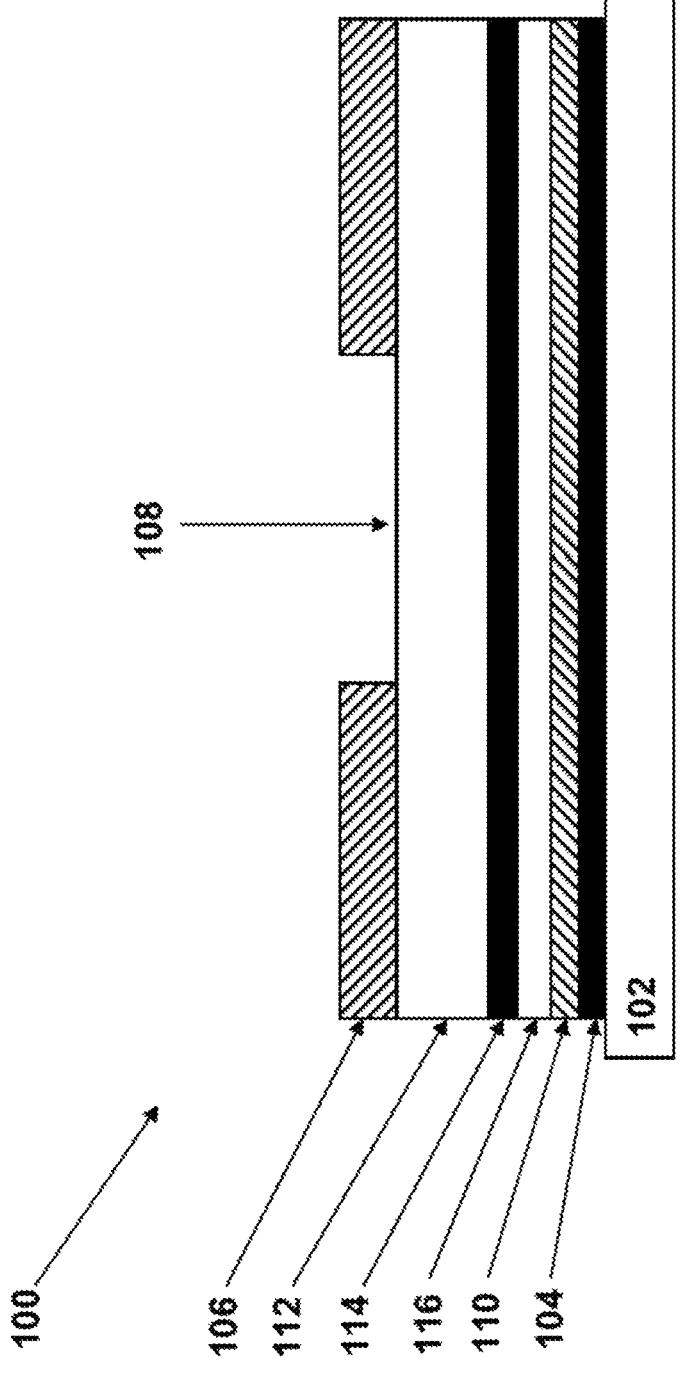
FIG. 2A provides a diagrammatic view of one embodiment of an amperometric analyte sensor to which an interference rejection membrane can be added.
Figure 2B:
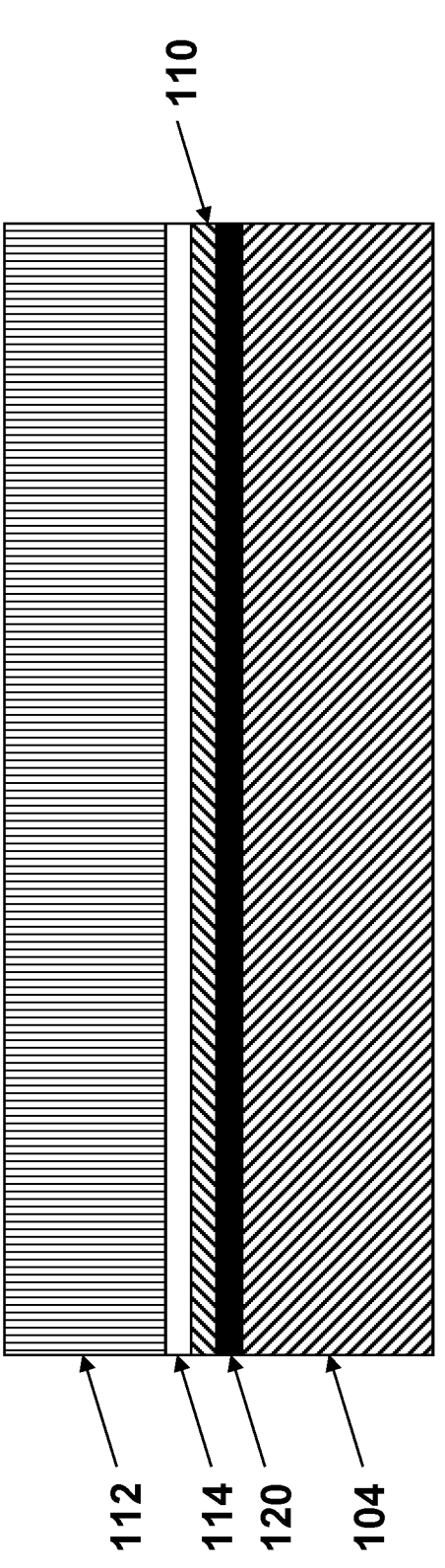
FIG. 2B provides a diagrammatic view of one embodiment of an amperometric analyte sensor having an interference rejection membrane.

Amperometric sensors typically comprise a plurality of layered elements including, for example, a base layer having an electrode, an enzyme layer, and an analyte diffusion control (e.g. glucose limiting) membrane. In some sensor embodiments, an adhesion promoter layer is added to facilitate close attachment of various layers such as a diffusion control membrane and enzyme layer. One such sensor embodiment is shown in FIG. 2A. Embodiments of the invention disclosed herein further include an interference rejection membrane (IRM) that is designed to inhibit and/or prevent endogenous or exogenous electroactive substances in vivo (e.g. in interstitial fluid). These endogenous or exogenous electroactive substances, such as acetaminophen, uric acid, and ascorbic acid, are inhibited and/or prevented from accessing the sensor electrode and being oxidized at the electrode surface, which would consequently produce a spurious signal that can confound measurements of the signal generated by the analyte to be measured. One illustrative embodiment of a sensor having an interference rejection membrane is shown in FIG. 2B.

Interference rejection membranes known in the art include, for example, those made from materials such as cellulose acetate, NAFION™ (a sulfonated tetrafluoroethylene based fluoropolymer-copolymer), and electropolymerized phenylene diamine. However, these membranes exhibit a number of material properties that make them unsuitable for use with certain types of sensors. For example, while cellulose acetate compositions can function as an interference rejection membrane if appropriately formulated, the interference rejection membrane needs to be thick, usually at least 5 micrometer to get a good rejection profile. Unfortunately, this thickness requirement can add undesirable bulk to implantable sensors and can also compromise sensor operability by inhibiting an analyte's ability to generate a signal. While NAFION™ membranes typically do not exhibit this problem, this material is not efficient at blocking interfering molecules including acetaminophen, a major interfering species in amperometric glucose sensors. In addition, electropolymerized films such as electropolymerized phenylene diamine tend to degrade relatively quickly, thereby compromising sensor lifetimes. U.S. Pat. No. 5,837,454 discloses a semi-permeable membrane made via a silane condensation reaction caused by hydrolysis of alkoxy groups to yield organosilicon hydroxides which condense to form poly(organosiloxanes). Unfortunately, interference rejection membranes formed this way do not function well when disposed on coarse surfaces such as the platinum black compositions that comprise certain electrode surfaces. In addition, interference rejection membranes formed this way are relatively hydrophobic, a property which contributes to undesirable phenomena in situations where in vivo analytes are being measured in an aqueous environment (e.g. the interstitial space). Such phenomena include, for example, slow sensor hydration profiles (i.e. slow sensor initialization/wet-up) and sensor signal drift. Thus, there are a number of problems with interference rejection membranes described in the art that make them unsuitable for use with a number of sensors described in the art (e.g. amperometric glucose sensors comprising platinum back electrode surfaces upon which a plurality of functional coatings are disposed). Consequently, there is a need in the art for interference rejection membranes having a constellation of versatile material properties that allow for their use in a variety of contexts.

The interference rejection membrane formulations and processes provided herein address such issues and also significantly improve sensor reliability. Embodiments of the interference rejection membranes disclosed herein comprise polymeric materials constructed to exhibit a constellation of material properties that can be used in a variety of contexts and for example, overcome a number of technical problems observed in sensors, such as electrochemical glucose sensors that are implanted in vivo and which utilize the chemical reaction between glucose and glucose oxidase to generate a measurable signal. Specifically, various embodiments of an interference rejecting membrane (IRM) is provided that retards the diffusion of interfering, electroactive compounds (such as acetaminophen, uric acid and ascorbic acid) relative to the diffusion of the $H_2O_2$ generated by enzyme reactions, which thereby eliminates the co-measurements of these interferents. Embodiments of the invention include membrane compositions that can be used for example in amperometric sensors (e.g. glucose sensors used by individuals suffering from diabetes) to inhibit spurious signals caused by interfering compounds. The interferents are prevented from reaching the anode during the current measuring period. This mechanism can be compared to chromatography, albeit the length of the column (which in this case is the thickness of the membrane) is very short.

In sensors that are implanted in vivo, embodiments of the interference rejection membrane function without requiring a thick material layer that substantially increases the bulk of the sensor or compromises sensor operability (e.g. by effecting stiochiometric ratios of diffusing physiological reactants). In addition, for sensors such as amperometric glucose sensors, the molecular structure of the interference rejection membrane material functions as a sort of molecular sieve that inhibits the diffusion of compounds having a molecular weight greater than 140 Daltons (e.g. so as to inhibit the diffusion of compounds/interferents such as acetaminophen, uric acid, ascorbic acid and the like, while simultaneously permitting the diffusion of smaller compounds such as hydrogen peroxide). In certain embodiments of the invention, the IRM inhibits the diffusion of interferents having a molecular weight greater than 150 Daltons. In one or more instances, the IRM inhibits the diffusion of acetaminophen, ascorbic acid, and/or uric acid there through to the electroactive surface of an electrode within an analyte sensor.

In addition to the above-noted material properties, in various embodiments, the molecular structure of the interference rejection membrane material is free of electrochemically reactive moieties that can for example, generate spurious signals at the surface of an electrode (either directly or indirectly). Moreover, for sensors that comprise a plurality of layered elements, in certain embodiments, the material of the interference rejection layer exhibits adhesive properties that allow it to adhere to coarse surfaces such as the platinum black compositions that comprise some electrode surfaces, while at the same time allow it to adhere to a variety of other matrices, for example adjacent layers comprising bioactive molecules such as glucose oxidase (i.e. so as to exhibit adhesive properties that inhibit delamination of the sensor layers).

In addition, sensors comprising a plurality of layers that are designed to measure analytes in aqueous environments (e.g. those implanted in vivo) typically require wetting of the layers prior to and during the measurement of accurate analyte reading. Because the properties of a material can influence the rate at which it hydrates, in various embodiments, the material properties of the interference rejection membrane used in aqueous environments facilitates sensor wetting to, for example, minimize the time period between the sensor's introduction into an aqueous environment and its ability to provide accurate signals that correspond to the concentrations of an analyte in that environment. In particular, embodiments of the invention comprise polymers crosslinked by hydrophilic compounds that meet this need by facilitating sensor hydration.

With electrochemical glucose sensors that utilize the chemical reaction between glucose and glucose oxidase to generate a measurable signal, various embodiments of the interference rejection membrane do not exacerbate (and in some instances, actually diminish) what is known in the art as the "oxygen deficit problem". Specifically, because glucose oxidase-based sensors require both oxygen ($O_2$) as well as glucose to generate a signal, the presence of an excess of oxygen relative to glucose, is necessary for the operation of a glucose oxidase-based glucose sensor. However, because the concentration of oxygen in subcutaneous tissue is much less than that of glucose, oxygen can be the limiting reactant in the reaction between glucose, oxygen, and glucose oxidase in a sensor—a situation which compromises the sensor's ability to produce a signal that is strictly dependent on the concentration of glucose. In this context, because the properties of a material can influence the rate at which compounds diffuse through that material to the site of a measurable chemical reaction, the material properties of the interference rejection membrane used in electrochemical glucose sensors that utilize the chemical reaction between glucose and glucose oxidase to generate a measurable signal, does not for example, favor the diffusion of glucose over oxygen in a manner that contributes to the oxygen deficit problem. For instance, embodiments of the invention that comprise methacrylate or primary amine polymers crosslinked by hydrophilic compounds do not contribute to the oxygen deficit problem.

In one aspect of the invention, the interference rejection membrane (IRM) comprises poly(vinyl alcohol) polymers. Polyvinyl alcohol (PVA or PVOH) has been used in the art as an effective binder for inorganic materials like clay, silica, and alumina. Positive attributes of PVA membranes include: excellent hydrophilicity, permeability to water, good mechanical properties, thermal resistance, resistance to chemicals, anti-fouling potential, low operating pressure, and film-forming ability. Disadvantages of PVA include: high degree of swelling, permeability to ions, compaction under pressure, and low flux when highly crosslinked.

PVA by itself and without crosslinking can be too hydrophilic (i.e. absorbing a lot of water and continually swelling). However, after crosslinking, PVA can form a very dense membrane structure while still maintaining good hydrophilicity. The hydrophilicity of PVA also provides a surprising advantage over current sensors in the art by eliminating the formation of bubbles on electrodes (e.g. counter electrodes), which avoids problems such as delamination and/or other membrane adhesion issues that occur with long-term use. This is due in part because the $H_2O_2$ permeability for hydrophilic membranes is higher than hydrophobic membranes. Multiple factors have an effect on crosslinking, including the heating temperature, heating time, crosslinker type and content, the PVA itself, molecular weight, degree of polymerization (DP), degree of hydrolysis (DH), and functional groups (e.g. —COOH, —SO3H, silanol).

Figure 3:
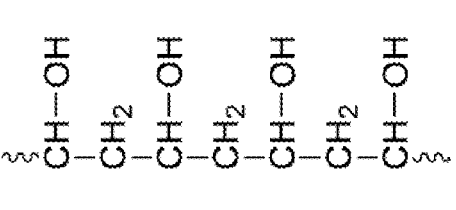
FIG. 3 provides a schematic of the esterification reaction occurring during the crosslinking of poly(vinyl alcohol) (PVA) polymers with dicarboxylic acid content monomers, in accordance with one or more embodiments of the invention.

In another aspect of the invention, the composition of the IRM comprises PVA polymers crosslinked by a crosslinker or crosslinking agent. Typically, the crosslinker is a dicarboxylic acid type monomer or a polymer comprising a carboxylic acid group inside of its individual units. In one or more embodiments, PVA is crosslinked through an esterification reaction by acids under various heating conditions (see, e.g. FIG. 3). Crosslinkers for PVA include, but are not limited to, sulfosuccinic acid (SSA), maleic acid, citric acid, oxalic acid, fumaric acid, poly(acrylic acid), poly(acrylic acid-co-maleic acid) (PAM), succinic acid, malonic acid, and poly(methyl vinyl ether-alt-maleic acid). In specific embodiments, PVA is crosslinked with an acid crosslinker selected from the group consisting of sulfosuccinic acid (SSA), maleic acid, citric acid, oxalic acid, fumaric acid, poly(acrylic acid), poly(acrylic acid-co-maleic acid) (PAM), succinic acid, malonic acid, and poly(methyl vinyl ether-alt-maleic acid). These crosslinked polymeric compositions may be used to coat a hydrogen peroxide transducing composition. An illustrative embodiment is a composition comprising an electrode (e.g. a platinum electrode used in an amperometric sensor) having an electroactive surface coated with, and in direct contact with a layer of PVA polymers crosslinked with sulfosuccinic acid or poly(methyl vinyl ether-alt-maleic acid).

Another variable consideration is the content of crosslinker in the mixture. In typical embodiments, 5% PVA is mixed with 10-20% crosslinker based on the PVA weight. In one preferred embodiment, the crosslinker is sulfosuccinic acid (SSA). The content of SSA may range from 5-30% of the PVA polymer weight. In one instance, the interference rejection membrane comprises 5 wt % poly(vinyl alcohol) crosslinked with 10 wt % sulfosuccinic acid. Illustrative embodiments include membranes made by mixing 5 g 5% PVA with 0.8 mL (~0.8 g) SSA(10%), and then heating this formulation at 130° C. for 40 minutes.

Figure 4:
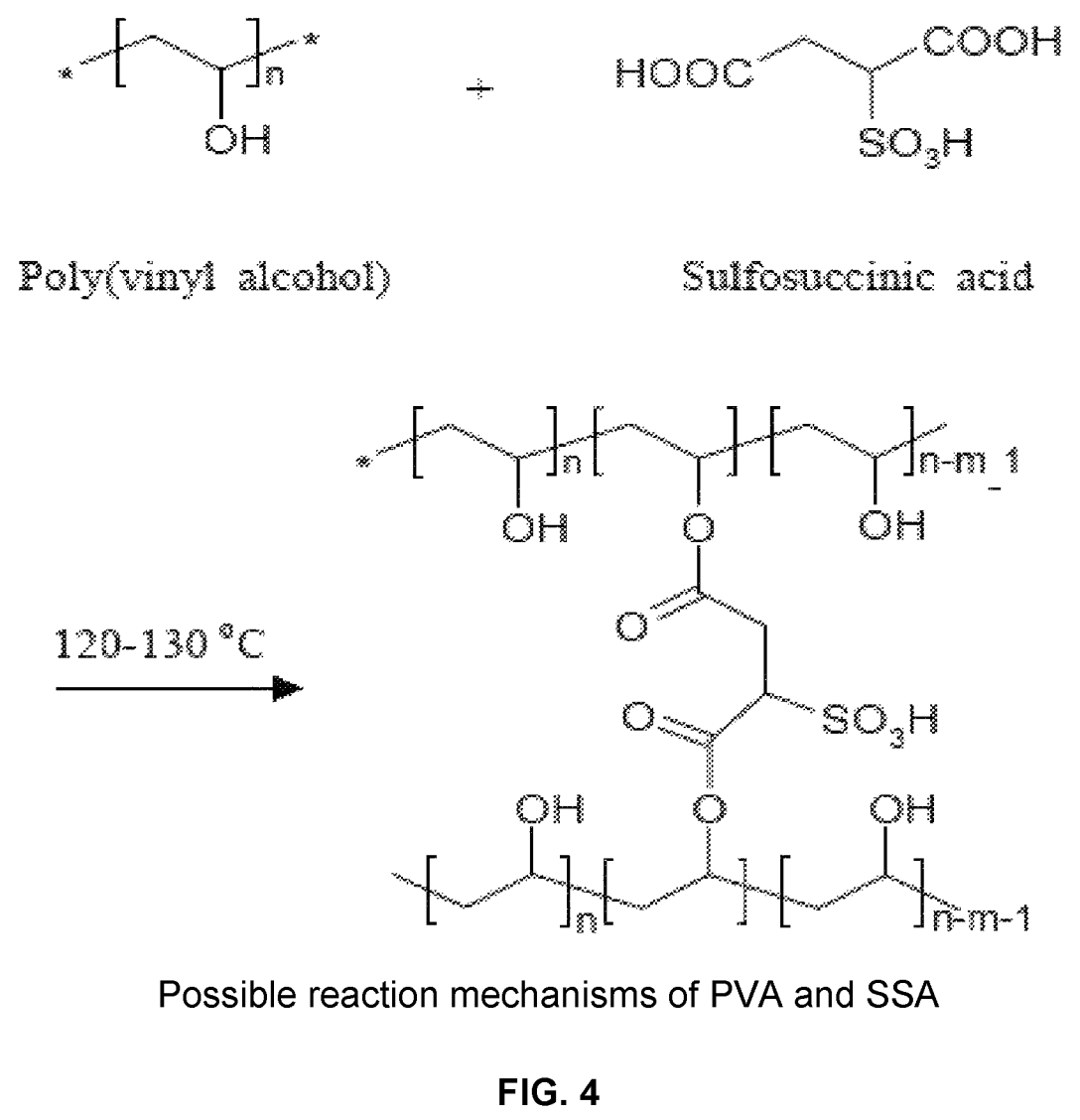

FIG. 4 illustrates a possible crosslinking reaction mechanism of PVA and SSA. Generally, a significant aspect of interference rejection (especially with acetaminophen) is based on a size exclusion principle which relies on a dense but thin membrane structure. By introducing an "—SO$_3$H" group to the polymer network through the crosslinking of PVA with SSA, the polymer becomes negatively charged at a pH greater than 7. This negative charge has an added advantage of further helping reject negatively-charged interference substances such as ascorbic acid, uric acid etc. In another preferred embodiment, the crosslinker is poly(methyl vinyl ether-alt-maleic acid).

In certain embodiments, PVA has a molecular weight (Mw) of at least 45K. A molecular weight greater than 45K is typically desired (generally the higher the Mw, the better). Generally, the PVA is a regular hydrolized PVA with a hydrolization degree of 88% to 99%. In certain embodiments of the invention, the degree of hydrolysis (DH) of the poly(vinyl alcohol) polymer is at least 98%. In specific instances, the DH is preferably 98%. In further embodiments, the PVA comprises a functional group, such as —COOH, —SO$_3$H or a silanized end group. In certain instances, a silanol functional PVA is used (e.g. Kuraray™ "R-polymer"). Such a polymer possesses a "silanol group" in its polymer chain and provides excellent binding strength and water resistance with a variety of inorganic materials. In one illustrative example, the silanol function PVA is a Kuraray™ Grade R-1130 "R-polymer", which is a standard powder with a viscosity (4% at 20° C.) of 20.0-30.0 mPa×s and a degree of hydrolysis of 98.0-99.0 mol %. In another illustrative example, the silanol function PVA is a Kuraray™ Grade NJE-190 "R-polymer", which is a fine powder (80 mesh pass) with a viscosity (4% at 20° C.) of 20.0-30.0 mPa×s and a degree of hydrolysis of 98.0-99.0 mol %.

The polymeric compositions of the invention can be formed using a variety of art-accepted processes. Typically, the interference rejection membrane is fabricated by a spray or spin-coating method, for example as a single or multi-layered coating over a substrate wafer. The polymers may be crosslinked, for example by exposing the polymers to a suitable crosslinking agent and then subjecting the crosslinking agent to a curing process such as heating them as described in the Examples section below. Process heating and membrane coating conditions include the spin coating RPM, the membrane thickness, as well as the heating temperature and the time period at the particular temperature. In certain instances, a curing temperature around 140° C. is preferred. In other instances, illustrative experiments have found that 400-500 RPM spin coating of the polymer solution and subsequently curing at 150° C. provides a better comprehensive result for certain embodiments.

In certain embodiments of the invention, such crosslinked polymers are adhered to a surface of an electrode that comprises an irregular architecture characteristic of an electrodeposition process (e.g. platinum black). In some embodiments, a first side of the interference rejection membrane is in direct contact with an electrochemically reactive surface of a working electrode; and an analyte sensing layer (e.g. one comprising glucose oxidase) is in direct contact with a second side of the interference rejection membrane.

The crosslinked polymer compositions disclosed herein allow the design of extremely thin interference rejection membranes that do not substantially increase the thickness of an existing sensor structure. Typically, the interference rejection membrane has a thickness of between 0.3 and 0.5, 1.0 or 2 μm, a thickness that allows them to be readily adapted for use with a variety of existing sensor designs without making substantial changes to these designs to accommodate this additional element. For example, in one illustrative embodiment of the invention, the interference rejection membrane is between 0.3-2 μm thick and formed on the electrode by a spin coating process at 400-1200 rpm and cured at a temperature between 130° C.-150° C. In preferred embodiments, the interference rejection membrane is between 0.4-0.8 μm thick. In one illustrative embodiment, the interference rejection membrane is between 0.4-0.8 μm thick and formed on the electrode by a spin coating process at 400-500 rpm and cured at a temperature of 130° C. for at least 40 minutes (e.g. 40-60 minutes). Following this heating crosslinking step, the membrane is rinsed in a bicarbonate buffer solution to effectively remove the excess amount of acid crosslinker added to the formulation, meanwhile provide some porosity to the small molecular such as H2O2 to pass through which were occupied by acid molecules. In a next step, the membrane is rinsed with water to remove all of the chemicals in previous rinse solutions.

Such a thin interference rejection membrane is used for example in implantable sensor embodiments of the invention to facilitate hydration of a sensor, as well as to inhibit the diffusion rate of compounds such as acetaminophen, ascorbic acid and uric acid therethrough while not substantially increasing the bulk of the implanted device (thereby decreasing the likelihood of a patient experiencing complications associated with implantation of the device). In certain embodiments, the interference rejection membrane inhibits the diffusion of acetaminophen therethrough in a manner that decreases a signal in the analyte sensor apparatus that results from a concentration of acetaminophen by at least 50% as compared to a control analyte sensor apparatus lacking the interference rejection membrane.

One illustrative embodiment of the invention is an amperometric analyte sensor apparatus (e.g. one designed for implantation within a mammal) comprising: a base layer; a conductive layer disposed on the base layer and comprising a working electrode; an interference rejection membrane disposed on an electroactive surface of the working electrode, wherein the interference rejection membrane comprises poly(vinyl alcohol) (PVA) polymers crosslinked by an acid crosslinker, wherein the crosslinker is a dicarboxylic acid type monomer or a polymer comprising a carboxylic acid group; and an analyte sensing layer; and an analyte sensing layer. Embodiments of the invention include a wide variety of sensor elements and configurations of elements. For example, in certain embodiments of the invention, the interference rejection membrane is in direct contact with an electrochemically reactive surface of the working electrode; and the analyte sensing layer is disposed on the interference rejection membrane. In some embodiments of the invention, the interference rejection membrane comprises a plurality of coatings of the polymeric material (e.g. coatings disposed on an electrode via a spray process as disclosed in the Examples section below).

Typically, the analyte sensing layer comprises an oxidoreductase (e.g. glucose oxidase) that generates hydrogen peroxide upon exposure to a substrate for the oxidoreductase (e.g. glucose), wherein the amount of hydrogen peroxide generated by the oxidoreductase is proportional to the amount of substrate exposed to the oxidoreductase. Optionally, such embodiments of the invention further include: a protein layer disposed on the analyte sensing layer; an analyte modulating layer disposed on the analyte sensing layer or the protein layer, wherein the analyte modulating layer comprises a composition that modulates the diffusion of an analyte such as glucose diffusing through the analyte modulating layer; an adhesion promoting layer disposed on the analyte sensing layer, wherein the adhesion promoting layer promotes the adhesion between the analyte sensing layer and an analyte modulating layer; or a cover layer disposed on the analyte sensor apparatus, wherein the cover layer comprises an aperture positioned on the cover layer so as to facilitate an analyte present in the mammal accessing and diffusing through an analyte modulating layer; and accessing the analyte sensing layer.

In some embodiments of the invention, the conductive layer comprises a plurality of electrodes including the working electrode, a counter electrode and a reference electrode. Optionally, the conductive layer comprises a plurality of working electrodes, counter electrodes and reference electrodes; and the plurality of working, counter, and reference electrodes are grouped together as a unit and positionally distributed on the conductive layer in a repeating pattern of units. In some embodiments of the invention, the sensor is operatively coupled to: a sensor input capable of receiving a signal from the sensor that is based on a sensed physiological characteristic value in the mammal; and a processor coupled to the sensor input, wherein the processor is capable of characterizing one or more signals received from the sensor. In certain embodiments of the invention, a pulsed voltage is used to obtain a signal from an electrode.

Another aspect of the invention is a method of making an analyte sensing system or sensor apparatus having the constellation of elements and/or made by the methodological steps disclosed herein. In one or more embodiments, the method comprises the steps of: providing a base layer; forming a conductive layer on the base layer, wherein the conductive layer includes a working electrode; forming an interference rejection membrane on the working electrode; forming an analyte sensing layer on the conductive layer, wherein the analyte sensing layer includes an oxidoreductase; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In one or more embodiments, the interference rejection membrane comprises poly(vinyl alcohol) polymers crosslinked with sulfosuccinic acid or poly(methyl vinyl ether-alt-maleic acid).

In illustrative experiments described in the Examples section below, embodiments of the interference rejection membrane have been found to have good hydrophilicity, which improved sensor start-up and in vivo performances without losing stability during the testing period. The interference rejection membranes were also shown to provide much better sensor selectivity in eliminating interference from other substances while still having the capability to maintain good performance characteristics, such as in dealing with $O_2$-effect related issues.

A. Typical Sensor Architectures Found in Embodiments of the Invention

FIG. 2A illustrates a cross-section of a typical sensor embodiment 100 of the present invention. This sensor embodiment is formed from a plurality of components that are typically in the form of layers of various conductive and non-conductive constituents disposed on each other according to art accepted methods and/or the specific methods of the invention disclosed herein. The components of the sensor are typically characterized herein as layers because, for example, it allows for a facile characterization of the sensor structure shown in FIG. 2. Artisans will understand however, that in certain embodiments of the invention, the sensor constituents are combined such that multiple constituents form one or more heterogeneous layers. In this context, those of skill in the art understand that the ordering of the layered constituents can be altered in various embodiments of the invention.

The embodiment shown in FIG. 2A includes a base layer 102 to support the sensor 100. The base layer 102 can be made of a material such as a metal and/or a ceramic and/or a polymeric substrate, which may be self-supporting or further supported by another material as is known in the art. Embodiments of the invention include a conductive layer 104 which is disposed on and/or combined with the base layer 102. Typically the conductive layer 104 comprises one or more electrodes. An operating sensor 100 typically includes a plurality of electrodes such as a working electrode, a counter electrode and a reference electrode. Other embodiments may also include a plurality of working and/or counter and/or reference electrodes and/or one or more electrodes that performs multiple functions, for example one that functions as both as a reference and a counter electrode.

As discussed in detail below, the base layer 102 and/or conductive layer 104 can be generated using many known techniques and materials. In certain embodiments of the invention, the electrical circuit of the sensor is defined by etching the disposed conductive layer 104 into a desired pattern of conductive paths. A typical electrical circuit for the sensor 100 comprises two or more adjacent conductive paths with regions at a proximal end to form contact pads and regions at a distal end to form sensor electrodes. An electrically insulating cover layer 106 such as a polymer coating can be disposed on portions of the sensor 100. Acceptable polymer coatings for use as the insulating protective cover layer 106 can include, but are not limited to, non-toxic biocompatible polymers such as silicone compounds, polyimides, biocompatible solder masks, epoxy acrylate copolymers, or the like. In the sensors of the present invention, one or more exposed regions or apertures 108 can be made through the cover layer 106 to open the conductive layer 104 to the external environment and to, for example, allow an analyte such as glucose to permeate the layers of the sensor and be sensed by the sensing elements. Apertures 108 can be formed by a number of techniques, including laser ablation, tape masking, chemical milling or etching or photolithographic development or the like. In certain embodiments of the invention, during manufacture, a secondary photoresist can also be applied to the protective layer 106 to define the regions of the protective layer to be removed to form the aperture(s) 108. The exposed electrodes and/or contact pads can also undergo secondary processing (e.g. through the apertures 108), such as additional plating processing, to prepare the surfaces and/or strengthen the conductive regions.

In the sensor configuration shown in FIG. 2A, an analyte sensing layer 110 (which is typically a sensor chemistry layer, meaning that materials in this layer undergo a chemical reaction to produce a signal that can be sensed by the conductive layer) is disposed on one or more of the exposed electrodes of the conductive layer 104. In the sensor configuration shown in FIG. 2B, an interference rejection membrane 120 is disposed on one or more of the exposed electrodes of the conductive layer 104, with the analyte sensing layer 110 then being disposed on this interference rejection membrane 120. Typically, the analyte sensing layer 110 is an enzyme layer. Most typically, the analyte sensing layer 110 comprises an enzyme capable of producing and/or utilizing oxygen and/or hydrogen peroxide, for example the enzyme glucose oxidase. Optionally, the enzyme in the analyte sensing layer is combined with a second carrier protein such as human serum albumin, bovine serum albumin or the like. In an illustrative embodiment, an oxidoreductase enzyme such as glucose oxidase in the analyte sensing layer 110 reacts with glucose to produce hydrogen peroxide, a compound which then modulates a current at an electrode. As this modulation of current depends on the concentration of hydrogen peroxide, and the concentration of hydrogen peroxide correlates to the concentration of glucose, the concentration of glucose can be determined by monitoring this modulation in the current. In a specific embodiment of the invention, the hydrogen peroxide is oxidized at a working electrode which is an anode (also termed herein the anodic working electrode), with the resulting current being proportional to the hydrogen peroxide concentration. Such modulations in the current caused by changing hydrogen peroxide concentrations can by monitored by any one of a variety of sensor detector apparatuses such as a universal sensor amperometric biosensor detector or one of the other variety of similar devices known in the art such as glucose monitoring devices produced by Medtronic™ MiniMed™.

In embodiments of the invention, the analyte sensing layer 110 can be applied over portions of the conductive layer or over the entire region of the conductive layer. Typically the analyte sensing layer 110 is disposed on the working electrode which can be the anode or the cathode. Optionally, the analyte sensing layer 110 is also disposed on a counter and/or reference electrode. While the analyte sensing layer 110 can be up to about 1000 microns ($\mu$m) in thickness, typically the analyte sensing layer is relatively thin as compared to those found in sensors previously described in the art, and is for example, typically less than 1, 0.5, 0.25 or 0.1 microns in thickness. As discussed in detail below, some methods for generating a thin analyte sensing layer 110 include brushing the layer onto a substrate (e.g. the reactive surface of a platinum black electrode), as well as spin coating processes, dip and dry processes, low shear spraying processes, ink-jet printing processes, silk screen processes and the like.

Typically, the analyte sensing layer 110 is coated and/or disposed next to one or more additional layers. Optionally, the one or more additional layers includes a protein layer 116 disposed upon the analyte sensing layer 110. Typically, the protein layer 116 comprises a protein such as human serum albumin, bovine serum albumin or the like. Typically, the protein layer 116 comprises human serum albumin. In some embodiments of the invention, an additional layer includes an analyte modulating layer 112 that is disposed above the analyte sensing layer 110 to regulate analyte access with the analyte sensing layer 110. For example, the analyte modulating membrane layer 112 can comprise a glucose limiting membrane, which regulates the amount of glucose that contacts an enzyme such as glucose oxidase that is present in the analyte sensing layer. Such glucose limiting membranes can be made from a wide variety of materials known to be suitable for such purposes, e.g., silicone compounds such as polydimethyl siloxanes, polyurethanes, polyurea cellulose acetates, NAFION, polyester sulfonic acids (e.g. Kodak AQ), hydrogels or any other suitable hydrophilic membranes known to those skilled in the art.

In typical embodiments of the invention, an adhesion promoter layer 114 is disposed between the analyte modulating layer 112 and the analyte sensing layer 110 as shown in FIG. 2 in order to facilitate their contact and/or adhesion. In a specific embodiment of the invention, an adhesion promoter layer 114 is disposed between the analyte modulating layer 112 and the protein layer 116 as shown in FIG. 2 in order to facilitate their contact and/or adhesion. The adhesion promoter layer 114 can be made from any one of a wide variety of materials known in the art to facilitate the bonding between such layers. Typically, the adhesion promoter layer 114 comprises a silane compound. In alternative embodiments, protein or like molecules in the analyte sensing layer 110 can be sufficiently crosslinked or otherwise prepared to allow the analyte modulating membrane layer 112 to be disposed in direct contact with the analyte sensing layer 110 in the absence of an adhesion promoter layer 114.

Embodiments of typical elements used to make the sensors disclosed herein are discussed below.

B. Typical Analyte Sensor Constituents Used in Embodiments of the Invention

The following disclosure provides examples of typical elements/constituents used in sensor embodiments of the invention. While these elements can be described as discreet units (e.g. layers), those of skill in the art understand that sensors can be designed to contain elements having a combination of some or all of the material properties and/or functions of the elements/constituents discussed below (e.g.

an element that serves both as a supporting base constituent and/or a conductive constituent and/or a matrix for the analyte sensing constituent and which further functions as an electrode in the sensor). Those in the art understand that these thin film analyte sensors can be adapted for use in a number of sensor systems such as those described herein.

Base Constituent

Sensors of the invention typically include a base constituent (see, e.g. element 102 in FIG. 2A). The term "base constituent" is used herein according to art accepted terminology and refers to the constituent in the apparatus that typically provides a supporting matrix for the plurality of constituents that are stacked on top of one another and comprise the functioning sensor. In one form, the base constituent comprises a thin film sheet of insulative (e.g. electrically insulative and/or water impermeable) material. This base constituent can be made of a wide variety of materials having desirable qualities such as dielectric properties, water impermeability and hermeticity. Some materials include metallic, and/or ceramic and/or polymeric substrates or the like.

The base constituent may be self-supporting or further supported by another material as is known in the art. In one embodiment of the sensor configuration shown in FIG. 2A, the base constituent 102 comprises a ceramic. Alternatively, the base constituent comprises a polymeric material such as a polyimmide. In an illustrative embodiment, the ceramic base comprises a composition that is predominantly $Al_2O_3$ (e.g. 96%). The use of alumina as an insulating base constituent for use with implantable devices is disclosed in U.S. Pat. Nos. 4,940,858, 4,678,868 and 6,472,122 which are incorporated herein by reference. The base constituents of the invention can further include other elements known in the art, for example hermetical vias (see, e.g. WO 03/023388). Depending upon the specific sensor design, the base constituent can be relatively thick constituent (e.g. thicker than 50, 100, 200, 300, 400, 500 or 1000 microns). Alternatively, one can utilize a nonconductive ceramic, such as alumina, in thin constituents, e.g., less than about 30 microns.

Conductive Constituent

The electrochemical sensors of the invention typically include a conductive constituent disposed upon the base constituent that includes at least one electrode for measuring an analyte or its byproduct (e.g. oxygen and/or hydrogen peroxide) to be assayed (see, e.g. element 104 in FIG. 2A). The term "conductive constituent" is used herein according to art accepted terminology and refers to electrically conductive sensor elements such as electrodes which are capable of measuring and a detectable signal and conducting this to a detection apparatus. An illustrative example of this is a conductive constituent that can measure an increase or decrease in current in response to exposure to a stimuli such as the change in the concentration of an analyte or its byproduct as compared to a reference electrode that does not experience the change in the concentration of the analyte, a coreactant (e.g. oxygen) used when the analyte interacts with a composition (e.g. the enzyme glucose oxidase) present in analyte sensing constituent 110 or a reaction product of this interaction (e.g. hydrogen peroxide). Illustrative examples of such elements include electrodes which are capable of producing variable detectable signals in the presence of variable concentrations of molecules such as hydrogen peroxide or oxygen. Typically one of these electrodes in the conductive constituent is a working electrode, which can be made from non-corroding metal or carbon. A carbon working electrode may be vitreous or graphitic and can be made from a solid or a paste. A metallic working electrode may be made from platinum group metals, including palladium or gold, or a non-corroding metallically conducting oxide, such as ruthenium dioxide. Alternatively the electrode may comprise a silver/silver chloride electrode composition. The working electrode may be a wire or a thin conducting film applied to a substrate, for example, by coating or printing. Typically, only a portion of the surface of the metallic or carbon conductor is in electrolytic contact with the analyte-containing solution. This portion is called the working surface of the electrode. The remaining surface of the electrode is typically isolated from the solution by an electrically insulating cover constituent 106. Examples of useful materials for generating this protective cover constituent 106 include polymers such as polyimides, polytetrafluoroethylene, polyhexafluoropropylene and silicones such as polysiloxanes.

In addition to the working electrode, the analyte sensors of the invention typically include a reference electrode or a combined reference and counter electrode (also termed a quasi-reference electrode or a counter/reference electrode). If the sensor does not have a counter/reference electrode then it may include a separate counter electrode, which may be made from the same or different materials as the working electrode. Typical sensors of the present invention have one or more working electrodes and one or more counter, reference, and/or counter/reference electrodes. One embodiment of the sensor of the present invention has two, three or four or more working electrodes. These working electrodes in the sensor may be integrally connected or they may be kept separate.

Typically for in vivo use, embodiments of the present invention are implanted subcutaneously in the skin of a mammal for direct contact with the body fluids of the mammal, such as blood. Alternatively the sensors can be implanted into other regions within the body of a mammal such as in the intraperotineal space. When multiple working electrodes are used, they may be implanted together or at different positions in the body. The counter, reference, and/or counter/reference electrodes may also be implanted either proximate to the working electrode(s) or at other positions within the body of the mammal. Embodiments of the invention include sensors comprising electrodes constructed from nanostructured materials. As used herein, a "nanostructured material" is an object manufactured to have at least one dimension smaller than 100 nm. Examples include, but are not limited to, single-walled nanotubes, double-walled nanotubes, multi-walled nanotubes, bundles of nanotubes, fullerenes, cocoons, nanowires, nanofibres, onions and the like.

Interference Rejection Constituent

The electrochemical sensors of the invention typically include an interference rejection constituent disposed between the surface of the electrode and the environment to be assayed. In particular, certain sensor embodiments rely on the oxidation and/or reduction of hydrogen peroxide generated by enzymatic reactions on the surface of a working electrode at a constant potential applied. Because amperometric detection based on direct oxidation of hydrogen peroxide requires a relatively high oxidation potential, sensors employing this detection scheme may suffer interference from oxidizable species that are present in biological fluids, such as ascorbic acid, uric acid and acetaminophen. In this context, the term "interference rejection constituent" is used herein according to art accepted terminology and refers to a coating or membrane in the sensor that functions to inhibit spurious signals generated by such oxidizable species which interfere with the detection of the signal generated by the analyte to be sensed. Certain interference rejection constituents function via size exclusion (e.g. by excluding interfering species of a specific size).

Typically, the interference rejection constituent comprises crosslinked poly(vinyl alcohol) (PVA) polymers. Other examples of interference rejection constituents include one or more layers or coatings of compounds such as the hydrophilic crosslinked pHEMA polymers, polylysine polymers, cellulose acetate (including cellulose acetate incorporating agents such as poly(ethylene glycol)), polyethersulfones, polytetra-fluoroethylenes, the perfluoronated ionomer NAFION™, polyphenylenediamine, epoxy and the like. Illustrative discussions of such interference rejection constituents are found for example in Ward et al., Biosensors and Bioelectronics 17 (2002) 181-189 and Choi et al., Analytical Chimica Acta 461 (2002) 251-260 which are incorporated herein by reference. Other interference rejection constituents include for example those observed to limit the movement of compounds based upon a molecular weight range, for example cellulose acetate as disclosed for example in U.S. Pat. No. 5,755,939, the contents of which are incorporated by reference.

Typically, the crosslinker is a dicarboxylic acid type monomer or a polymer comprising a carboxylic acid group. In certain instances, the crosslinker is sulfosuccinic acid (SSA), which has been demonstrated to be a very efficient crosslinker suitable for use with PVA. In another instance, the crosslinker is poly(methyl vinyl ether-alt-maleic acid), which has also been found to be suitable for use with PVA. Other suitable crosslinkers include maleic acid, citric acid, oxalic acid, fumaric acid, poly(acrylic acid), poly(acrylic acid-co-maleic acid) (PAM), succinic acid, and malonic acid.

In certain embodiments of the invention, the specific placement of the interference rejection membrane element relative to other sensor elements is used to effect its function. For example, in sensor embodiments where the disclosed crosslinked polymeric compositions are disposed directly on the electroactive surface of the electrode, they function to provide size-exclusion based interference rejection membranes, ones which inhibit the diffusion of interfering species while simultaneously allowing $H_2O_2$ produced from an analyte enzyme reaction to access the electrode and generate an appropriate signal. Moreover, as noted above, poly(vinyl alcohol) (PVA) polymers crosslinked by an acid crosslinker further provides an optimized hydrophilic environment so as to expedite the sensor initial hydration speed. Such polymers also offer a compatible matrix for a subsequent layer such as an enzyme layer (e.g. one comprising glucose oxidase) to be adhered to. Consequently, the crosslinked polymeric compositions disclosed herein exhibit a surprising constellation of material properties that make them ideal for use with certain sensor designs (e.g. implantable amperometric glucose sensors comprising a platinum back electrode surfaces upon which a plurality of functional coatings are disposed). This unexpected constellation of material properties includes, for example, an ability to facilitate sensor hydration (thereby decreasing start-up time), an ability to facilitate adhesion of the sensor layers so as to provide a stabilized sensor (and output signal) as well as an ability to inhibit spurious sensor signals caused by interfering species during sensor operation.

Additional compositions having an unexpected constellation of material properties that make them ideal for use as interference rejection membranes in certain amperometric glucose sensors as well as methods for making and using them are further disclosed herein.

Analyte Sensing Constituent

The electrochemical sensors of the invention include an analyte sensing constituent disposed on the electrodes of the sensor (see, e.g. element 110 in FIG. 2A). The term "analyte sensing constituent" is used herein according to art accepted terminology and refers to a constituent comprising a material that is capable of recognizing or reacting with an analyte whose presence is to be detected by the analyte sensor apparatus. Typically this material in the analyte sensing constituent produces a detectable signal after interacting with the analyte to be sensed, typically via the electrodes of the conductive constituent. In this regard the analyte sensing constituent and the electrodes of the conductive constituent work in combination to produce the electrical signal that is read by an apparatus associated with the analyte sensor. Typically, the analyte sensing constituent comprises an oxidoreductase enzyme capable of reacting with and/or producing a molecule whose change in concentration can be measured by measuring the change in the current at an electrode of the conductive constituent (e.g. oxygen and/or hydrogen peroxide), for example the enzyme glucose oxidase. An enzyme capable of producing a molecule such as hydrogen peroxide can be disposed on the electrodes according to a number of processes known in the art. The analyte sensing constituent can coat all or a portion of the various electrodes of the sensor. In this context, the analyte sensing constituent may coat the electrodes to an equivalent degree. Alternatively the analyte sensing constituent may coat different electrodes to different degrees, with, for example, the coated surface of the working electrode being larger than the coated surface of the counter and/or reference electrode.

Typical sensor embodiments of this element of the invention utilize an enzyme (e.g. glucose oxidase) that has been combined with a second protein (e.g. albumin) in a fixed ratio (e.g. one that is typically optimized for glucose oxidase stabilizing properties) and then applied on the surface of an electrode to form a thin enzyme constituent. In a typical embodiment, the analyte sensing constituent comprises a GOx and HSA mixture. In a typical embodiment of an analyte sensing constituent having GOx, the GOx reacts with glucose present in the sensing environment (e.g. the body of a mammal) and generates hydrogen peroxide according to the reaction shown in FIG. 1, wherein the hydrogen peroxide so generated is anodically detected at the working electrode in the conductive constituent.

As noted above, the enzyme and the second protein (e.g. an albumin) are typically treated to form a crosslinked matrix (e.g. by adding a cross-linking agent to the protein mixture). As is known in the art, crosslinking conditions may be manipulated to modulate factors such as the retained biological activity of the enzyme, its mechanical and/or operational stability. Illustrative crosslinking procedures are described in U.S. patent application Ser. No. 10/335,506 and PCT publication WO 03/035891 which are incorporated herein by reference. For example, an amine cross-linking reagent, such as, but not limited to, glutaraldehyde, can be added to the protein mixture.

Protein Constituent

The electrochemical sensors of the invention optionally include a protein constituent disposed between the analyte sensing constituent and the analyte modulating constituent (see, e.g. element 116 in FIG. 2A). The term "protein constituent" is used herein according to art accepted terminology and refers to a constituent containing a carrier protein or the like that is selected for compatibility with the analyte sensing constituent and/or the analyte modulating constituent. In typical embodiments, the protein constituent comprises an albumin such as human serum albumin. The HSA concentration may vary between about 0.5%-30% (w/v). Typically the HSA concentration is about 1-10% w/v, and most typically is about 5% w/v. In alternative embodiments of the invention, collagen or BSA or other structural proteins used in these contexts can be used instead of or in addition to HSA. This constituent is typically crosslinked on the analyte sensing constituent according to art accepted protocols.

Adhesion Promoting Constituent

The electrochemical sensors of the invention can include one or more adhesion promoting (AP) constituents (see, e.g. element 114 in FIG. 2A). The term "adhesion promoting constituent" is used herein according to art accepted terminology and refers to a constituent that includes materials selected for their ability to promote adhesion between adjoining constituents in the sensor. Typically, the adhesion promoting constituent is disposed between the analyte sensing constituent and the analyte modulating constituent. Typically, the adhesion promoting constituent is disposed between the optional protein constituent and the analyte modulating constituent. The adhesion promoter constituent can be made from any one of a wide variety of materials known in the art to facilitate the bonding between such constituents and can be applied by any one of a wide variety of methods known in the art. Typically, the adhesion promoter constituent comprises a silane compound such as γ-aminopropyltrimethoxysilane.

The use of silane coupling reagents, especially those of the formula $R'Si(OR)_3$ in which $R'$ is typically an aliphatic group with a terminal amine and R is a lower alkyl group, to promote adhesion is known in the art (see, e.g. U.S. Pat. No. 5,212,050 which is incorporated herein by reference). For example, chemically modified electrodes in which a silane such as γ-aminopropyltriethoxysilane and glutaraldehyde were used in a step-wise process to attach and to co-crosslink bovine serum albumin (BSA) and glucose oxidase $(GO_x)$ to the electrode surface are well known in the art (see, e.g. Yao, T. Analytica Chim. Acta 1983, 148, 27-33).

In certain embodiments of the invention, the adhesion promoting constituent further comprises one or more compounds that can also be present in an adjacent constituent such as the polydimethyl siloxane (PDMS) compounds that serves to limit the diffusion of analytes such as glucose through the analyte modulating constituent. In illustrative embodiments the formulation comprises 0.5-20% PDMS, typically 5-15% PDMS, and most typically 10% PDMS. In certain embodiments of the invention, the adhesion promoting constituent is crosslinked within the layered sensor system and correspondingly includes an agent selected for its ability to crosslink a moiety present in a proximal constituent such as the analyte modulating constituent. In illustrative embodiments of the invention, the adhesion promoting constituent includes an agent selected for its ability to crosslink an amine or carboxyl moiety of a protein present in a proximal constituent such as the analyte sensing constituent and/or the protein constituent and/or a siloxane moiety present in a compound disposed in a proximal layer such as the analyte modulating layer.

Analyte Modulating Constituent

The electrochemical sensors of the invention include an analyte modulating constituent disposed on the sensor (see, e.g. element 112 in FIG. 2A). The term "analyte modulating constituent" is used herein according to art accepted terminology and refers to a constituent that typically forms a membrane on the sensor that operates to modulate the diffusion of one or more analytes, such as glucose, through the constituent. In certain embodiments of the invention, the analyte modulating constituent is an analyte-limiting membrane (e.g. a glucose limiting membrane) which operates to prevent or restrict the diffusion of one or more analytes, such as glucose, through the constituents. In other embodiments of the invention, the analyte-modulating constituent operates to facilitate the diffusion of one or more analytes, through the constituents. Optionally such analyte modulating constituents can be formed to prevent or restrict the diffusion of one type of molecule through the constituent (e.g. glucose), while at the same time allowing or even facilitating the diffusion of other types of molecules through the constituent (e.g. $O_2$).

With respect to glucose sensors, in known enzyme electrodes, glucose and oxygen from blood, as well as some interferents, such as ascorbic acid and uric acid, diffuse through a primary membrane of the sensor. As the glucose, oxygen and interferents reach the analyte sensing constituent, an enzyme, such as glucose oxidase, catalyzes the conversion of glucose to hydrogen peroxide and gluconolactone. The hydrogen peroxide may diffuse back through the analyte modulating constituent, or it may diffuse to an electrode where it can be reacted to form oxygen and a proton to produce a current that is proportional to the glucose concentration. The sensor membrane assembly serves several functions, including selectively allowing the passage of glucose therethrough. In this context, an illustrative analyte modulating constituent is a semi-permeable membrane which permits passage of water, oxygen and at least one selective analyte and which has the ability to absorb water, the membrane having a water soluble, hydrophilic polymer.

A variety of illustrative analyte modulating compositions are known in the art and are described for example in U.S. Pat. Nos. 6,319,540, 5,882,494, 5,786,4395,777,060, 5,771,868 and 5,391,250, the disclosures of each being incorporated herein by reference. The hydrogels described therein are particularly useful with a variety of implantable devices for which it is advantageous to provide a surrounding water constituent. In some embodiments of the invention, the analyte modulating composition includes PDMS. In certain embodiments of the invention, the analyte modulating constituent includes an agent selected for its ability to crosslink a siloxane moiety present in a proximal constituent. In closely related embodiments of the invention, the adhesion promoting constituent includes an agent selected for its ability to crosslink an amine or carboxyl moiety of a protein present in a proximal constituent.

Cover Constituent

The electrochemical sensors of the invention include one or more cover constituents which are typically electrically insulating protective constituents (see, e.g. element 106 in FIG. 2A). Typically, such cover constituents can be in the form of a coating, sheath or tube and are disposed on at least a portion of the analyte modulating constituent. Acceptable polymer coatings for use as the insulating protective cover constituent can include, but are not limited to, non-toxic biocompatible polymers such as silicone compounds, polyimides, biocompatible solder masks, epoxy acrylate copolymers, or the like. Further, these coatings can be photoimageable to facilitate photolithographic forming of apertures through to the conductive constituent. A typical cover constituent comprises spun on silicone. As is known in the art, this constituent can be a commercially available RTV (room temperature vulcanized) silicone composition. A typical chemistry in this context is polydimethyl siloxane (acetoxy based).

C. Typical Analyte Sensor System Embodiments of the Invention

Embodiments of the sensor elements and sensors disclosed herein can be operatively coupled to a variety of other systems elements typically used with analyte sensors (e.g. structural elements such as piercing members, insertion sets and the like as well as electronic components such as processors, monitors, medication infusion pumps and the like), for example to adapt them for use in various contexts (e.g. implantation within a mammal). One embodiment of the invention includes a method of monitoring a physiological characteristic of a user using an embodiment of the invention that includes an input element capable of receiving a signal from a sensor that is based on a sensed physiological characteristic value of the user, and a processor for analyzing the received signal. In typical embodiments of the invention, the processor determines a dynamic behavior of the physiological characteristic value and provides an observable indicator based upon the dynamic behavior of the physiological characteristic value so determined. In some embodiments, the physiological characteristic value is a measure of the concentration of blood glucose in the user. In other embodiments, the process of analyzing the received signal and determining a dynamic behavior includes repeatedly measuring the physiological characteristic value to obtain a series of physiological characteristic values in order to, for example, incorporate comparative redundancies into a sensor apparatus in a manner designed to provide confirmatory information on sensor function, analyte concentration measurements, the presence of interferences and the like.

Embodiments of the invention include devices which display data from measurements of a sensed physiological characteristic (e.g. blood glucose concentrations) in a manner and format tailored to allow a user of the device to easily monitor and, if necessary, modulate the physiological status of that characteristic (e.g. modulation of blood glucose concentrations via insulin administration). An illustrative embodiment of the invention is a device comprising a sensor input capable of receiving a signal from a sensor, the signal being based on a sensed physiological characteristic value of a user; a memory for storing a plurality of measurements of the sensed physiological characteristic value of the user from the received signal from the sensor; and a display for presenting a text and/or graphical representation of the plurality of measurements of the sensed physiological characteristic value (e.g. text, a line graph or the like, a bar graph or the like, a grid pattern or the like or a combination thereof). Typically, the graphical representation displays real time measurements of the sensed physiological characteristic value. Such devices can be used in a variety of contexts, for example in combination with other medical apparatuses. In some embodiments of the invention, the device is used in combination with at least one other medical device (e.g. a glucose sensor).

An illustrative system embodiment consists of a glucose sensor, a transmitter and pump receiver and a glucose meter. In this system, radio signals from the transmitter can be sent to the pump receiver periodically (e.g. every 5 minutes) to provide providing real-time sensor glucose (SG) values. Values/graphs are displayed on a monitor of the pump receiver so that a user can self monitor blood glucose and deliver insulin using their own insulin pump. Typically, an embodiment of device disclosed herein communicates with a second medical device via a wired or wireless connection. Wireless communication can include, for example, the reception of emitted radiation signals as occurs with the transmission of signals via RF telemetry, infrared transmissions, optical transmission, sonic and ultrasonic transmissions and the like. Optionally, the device is an integral part of a medication infusion pump (e.g. an insulin pump). Typically in such devices, the physiological characteristic values includes a plurality of measurements of blood glucose.

D. Embodiments of the Invention and Associated Characteristics

Embodiments of the invention disclosed herein focus on implantable analyte sensors and sensor systems that are designed to include hydrophilic compositions (e.g. an interference rejection membrane comprising polymers crosslinked by a hydrophilic crosslinking agent) and/or configurations of elements that facilitate sensor initialization and/or start-up in vivo (e.g. the run-in time that it takes for a sensor to settle into its aqueous environment and start transmitting meaningful information after being implanted in vivo). In particular, it is known in the art that the amount time required for sensor initialization and/or start-up prior to its use can be relatively long (e.g. in amperometric glucose sensors, the sensor start-up initialization times can range from 2 to 10 hours), a factor which can hinder the use of such sensors in the administration of medical care. For example, in hospital settings, a relatively long sensor initialization and/or start-up period can delay the receipt of important information relating to patient health (e.g. hyperglycemia or hypoglycemia in a diabetic patient), thereby delaying treatments predicated on the receipt of such information (e.g. the administration of insulin). In addition, a relatively long sensor initialization and/or start-up period in hospital settings can require repeated monitoring by hospital staff, a factor which contributes to the costs of patient care. For these reasons, sensors having reduced initialization and/or start-up times in vivo in hospital settings and sensors and sensor systems that are designed to include elements and/or configurations of elements that diminish long sensor initialization and/or start-up times are highly desirable. With glucose sensors for example, a 15-30 minute reduction of sensor initialization and/or start-up time is highly desirable because, for example, such shorter initialization times can: (1) reduce the need for patient monitoring by hospital personnel, a factor which contributes to the cost-effectiveness of such medical devices; and (2) reduce delays in the receipt of important information relating to patient health.

In individuals using analyte sensors in non-hospital settings (e.g. diabetics using glucose sensors to manage their disease), relatively long sensor initialization and/or start-up periods are also problematical due to both the inconvenience to the user as well as the delayed receipt of information relating to user health. The use of glucose sensors, insulin infusion pumps and the like in the management of diabetes has increased in recent years due for example to studies showing that the morbidity and mortality issues associated with this chronic disease decrease dramatically when a patient administers insulin in a manner that closely matches the rise and fall of physiological insulin concentrations in healthy individuals. Consequently, patients who suffer from chronic diseases such as diabetes are instructed by medical personnel to play an active role in the management of their disease, in particular, the close monitoring and modulation of blood glucose levels. In this context, because many diabetics do not have medical training, they may forgo optimal monitoring and modulation of blood glucose levels due to complexities associated with such management, for example, a two hour start-up period which can be an inconvenience in view of a patient's active daily routine. For these reasons, sensors and sensor systems that are designed to include elements and/or configurations of elements can reduce sensor initialization and/or start-up times (e.g. the hydrophilic interference rejection membranes disclosed herein) are highly desirable in situations where such sensors are operated by a diabetic patient without medical training because they facilitate the patient's convenient management of their disease, behavior which is shown to decrease the well known morbidity and mortality issues observed in individuals suffering from chronic diabetes.

While the analyte sensor and sensor systems disclosed herein are typically designed to be implantable within the body of a mammal, the inventions disclosed herein are not limited to any particular environment and can instead be used in a wide variety of contexts, for example for the analysis of most in vivo and in vitro liquid samples including biological fluids such as interstitial fluids, whole-blood, lymph, plasma, serum, saliva, urine, stool, perspiration, mucus, tears, cerebrospinal fluid, nasal secretion, cervical or vaginal secretion, semen, pleural fluid, amniotic fluid, peritoneal fluid, middle ear fluid, joint fluid, gastric aspirate or the like. In addition, solid or desiccated samples may be dissolved in an appropriate solvent to provide a liquid mixture suitable for analysis.

The invention disclosed herein has a number of embodiments. One illustrative embodiment of the invention is an analyte sensor apparatus comprising: an elongated (i.e. having notably more length than width) base layer; a conductive layer disposed on the base layer and comprising a reference electrode, a working electrode and a counter electrode; an interference rejection membrane disposed upon the conductive layer, an analyte sensing layer disposed on the interference rejection membrane; an analyte modulating layer disposed on the analyte sensing layer, wherein the analyte modulating layer comprises a composition that modulates the diffusion of an analyte diffusing through the analyte modulating layer; and a cover layer disposed on the analyte sensor apparatus, wherein the cover layer comprises an aperture positioned on the cover layer so as to facilitate an analyte accessing and diffusing through the analyte modulating layer and accessing the analyte sensing layer. Typical embodiments of the invention are comprised of biocompatible materials and/or have structural features designed for implantation within a mammal. Methodological embodiments of the invention include methods for making and using the sensor embodiments disclosed herein. Certain embodiments of the invention include methods of using a specific sensor element and/or a specific constellation of sensor elements to produce and/or facilitate one or more functions of the sensor embodiments disclosed herein.

As disclosed herein, those of skill in the art understand that a conductive layer disposed on the base layer and comprising a working electrode, a counter electrode and a reference electrode includes embodiments wherein the conductive layer is disposed on at least a portion the base layer and does not necessarily completely cover the base layer. Those of skill in the art will understand that this refers to other layers within the sensor, with for example, an analyte sensing layer disposed on the conductive layer encompassing sensor embodiments where the analyte sensing layer disposed on at least a portion of the conductive layer; and an analyte modulating layer disposed on the analyte sensing layer encompassing an analyte modulating layer disposed on at least a portion of the analyte sensing layer etc. Optionally, the electrodes can be disposed on a single surface or side of the sensor structure. Alternatively, the electrodes can be disposed on a multiple surfaces or sides of the sensor structure (and can for example be connected by vias through the sensor material(s) to the surfaces on which the electrodes are disposed). In certain embodiments of the invention, the reactive surfaces of the electrodes are of different relative areas/sizes, for example a 1× reference electrode, a 2.6× working electrode and a 3.6× counter electrode.

In certain embodiments of the invention, an element of the apparatus such as an electrode or an aperture is designed to have a specific configuration and/or is made from a specific material and/or is positioned relative to the other elements so as to facilitate a function of the sensor. For example, without being bound by a specific theory or mechanism of action, it appears that sensor embodiments (e.g. simple three electrode embodiments) may be more susceptible to local environment changes around a single electrode. For example, a gas bubble on top of or close to a reference or another electrode, and/or a stagnating or semi-stagnating pool of fluid on top of or close to a reference or another electrode may consequently compromises sensor performance. In this context, a distributed electrode configuration appears be advantageous because the distribution of the electrode area allows the sensor to compensate for signal lost to a small local area (e.g. as can occur due to lack of hydration, fluid stagnation, a patient's immune response, or the like).

Typical analyte sensor apparatus embodiments comprise a plurality of working electrodes, counter electrodes and reference electrodes. Optionally, the plurality of working, counter and reference electrodes are grouped together as a unit and positionally distributed on the conductive layer in a repeating pattern of units. Alternatively, the plurality of working, counter and reference electrodes are grouped together and positionally distributed on the conductive layer in a non-repeating pattern of units. In certain embodiments of the invention, the elongated base layer is made from a material that allows the sensor to twist and bend when implanted in vivo; and the electrodes are grouped in a configuration that facilitates an in vivo fluid accessing at least one of working electrode as the sensor apparatus twists and bends when implanted in vivo. In some embodiments, the electrodes are grouped in a configuration that allows the sensor to continue to maintain an optimal function if a portion of the sensor having one or more electrodes is dislodged from an in vivo environment and exposed to an ex vivo environment.

Optionally, embodiments of the invention include a plurality of working electrodes and/or counter electrodes and/or reference electrodes (e.g. to provide redundant sensing capabilities). Such embodiments of the invention can be used in embodiments of the invention that include a processor (e.g. one linked to a program adapted for a signal subtraction/cancellation process) are designed factor out background signals in vivo, for example by comparing signal(s) at GOx coated working electrode with signal at working electrode not coated with GOx (e.g. background detection followed by a signal subtraction/cancellation process to arrive at a true signal). Certain of these embodiments of the invention are particularly useful for sensing glucose at the upper and lower ends of the glucose signal curves. Similar embodiments of the invention are used to factor out interference, for example by comparing signal(s) at GOx coated working electrode with signal at working electrode not coated with GOx. Embodiments of the invention can include a coating of a Prussian blue composition on an electrode at a location and in an amount sufficient to mediate an electrical potential of an electrode of the apparatus. Related embodiments of the invention include methods for mediating an electrical potential of an electrode of the disclosed sensor apparatus (e.g. by using a Prussian blue composition). Prussian Blue formulas are known in the art and include Fe4[Fe(CN6]3×H2O, CI no. 77510 and KFe[Fe(Cn)6]×H2O id CI no. 77520.

In typical embodiments of the invention, the sensor is operatively coupled to further elements (e.g. electronic components) such as elements designed to transmit and/or receive a signal, monitors, pumps, processors and the like. For example, in some embodiments of the invention, the sensor is operatively coupled to a sensor input capable of receiving a signal from the sensor that is based on a sensed physiological characteristic value in the mammal; and a processor coupled to the sensor input, wherein the processor is capable of characterizing one or more signals received from the sensor. A wide variety of sensor configurations as disclosed herein can be used in such systems. Optionally, for example, the sensor comprises three working electrodes, one counter electrode and one reference electrode. In certain embodiments, at least one working electrode is coated with an analyte sensing layer comprising glucose oxidase (and optionally two are coated with GOx) and at least one working electrode is not coated with an analyte sensing layer comprising glucose oxidase. Such embodiments of the invention can be used for example in sensor embodiments designed factor out background signals in vivo, for example by comparing signal(s) at GOx coated working electrode(s) with signal at working electrode(s) not coated with GOx (e.g. background detection followed by a signal subtraction/cancellation process to arrive at a true signal).

In some embodiments of sensors insertion set apparatuses, a first and a second (and/or third etc.) electrochemical sensor comprises one working, counter and reference electrode. Alternatively, the plurality of electrochemical sensors comprise a plurality of working, counter and reference electrodes, for example those having a distributed configuration as disclosed in U.S. patent application Ser. No. 11/633,254, the contents of which are incorporated by reference. In certain embodiments of the invention, at least two in the plurality of sensors are designed to measure a signal generated by the same physiological characteristic, for example blood glucose concentration. Embodiments of the invention can include, for example, a plurality of electrochemical sensors having a working electrode coated with an oxidoreductase such as glucose oxidase and are used in methods designed to sample and compare glucose concentrations observed at the plurality of in vivo insertion sites. Alternatively, at least two in the plurality of sensors in the sensor apparatus are designed to measure signals generated by the different characteristics, for example a first characteristic comprising a background or interfering signal that is unrelated to blood glucose (e.g. "interferent noise") and a second characteristic comprising blood glucose concentrations. In an illustrative embodiment of this invention, a first sensor is designed to measure glucose oxidase and comprises one or more working electrodes coated with glucose oxidase while a second comparative sensor is designed to measure a background or interfering signal that is unrelated to blood glucose has no working electrode (or electrodes) coated with glucose oxidase.

In certain embodiments of the invention, sensor systems that utilize voltage pulsing and/or switching as disclosed herein are used in methods designed to overcome problems that can occur with implantable sensors and sensor systems due to lack of hydration (e.g. slow start-up initialization times) and/or fluid stagnation by enhancing the ability of a fluid to flow around the implanted components in a manner that inhibits the likelihood of a gas bubble or a stagnating pool of fluid from forming and/or remaining on top of or close to an electrode in a manner that compromises sensor function. In addition, embodiments of the invention that utilize voltage pulsing and/or switching can be combined with certain complementary elements disclosed herein so as to further overcome problems that result from a lack of hydration, fluid stagnation, a patient's immune response, or the like (e.g. distributed electrode configurations, multiple electrode sensors, multiple sensor apparatuses having multiple implantation sites, etc.).

In some embodiments of the invention, a processor is capable of comparing a first signal received from a working electrode in response to a first working potential with a second signal received from a working electrode in response to a second working potential, wherein the comparison of the first and second signals at the first and second working potentials can be used to identify a signal generated by an interfering compound. In one such embodiment of the invention, one working electrode is coated with glucose oxidase and another is not, and the interfering compound is acetaminophen, ascorbic acid, bilirubin, cholesterol, creatinine, dopamine, ephedrine, ibuprofen, L-dopa, methyldopa, salicylate, tetracycline, tolazamide, tolbutamide, triglycerides or uric acid. Optionally, a pulsed and/or varied (e.g. switched) voltage is used to obtain a signal from a working electrode. Typically, at least one voltage is 280, 535 or 635 millivolts. Related embodiments of the invention include methods for identifying and/or characterizing one or more signals generated by an interfering compound in various sensor embodiments of the invention (e.g. by comparing the signal from an electrode coated with an analyte sensing compound with a comparative electrode not coated with an analyte sensing compound). Optionally, such methods use a pulsed and/or varied working potential to observe a signal at an electrode.

Sensors of the invention can also be incorporated in a wide variety of medical systems known in the art. Sensors of the invention can be used, for example, in a closed loop infusion systems designed to control the rate that medication is infused into the body of a user. Such a closed loop infusion system can include a sensor and an associated meter which generates an input to a controller which in turn operates a delivery system (e.g. one that calculates a dose to be delivered by a medication infusion pump). In such contexts, the meter associated with the sensor may also transmit commands to, and be used to remotely control, the delivery system. Typically, the sensor is a subcutaneous sensor in contact with interstitial fluid to monitor the glucose concentration in the body of the user, and the liquid infused by the delivery system into the body of the user includes insulin. Illustrative systems are disclosed for example in U.S. Pat. Nos. 6,558,351 and 6,551,276; PCT Application Nos. US99/21703 and US99/22993; as well as WO 2004/008956 and WO 2004/009161, all of which are incorporated herein by reference.

Certain embodiments of the invention measure peroxide and have the advantageous characteristic of being suited for implantation in a variety of sites in the mammal including regions of subcutaneous implantation and intravenous implantation as well as implantation into a variety of non-vascular regions. A peroxide sensor design that allows implantation into non-vascular regions has advantages over certain sensor apparatus designs that measure oxygen due to the problems with oxygen noise that can occur in oxygen sensors implanted into non-vascular regions. For example, in such implanted oxygen sensor apparatus designs, oxygen noise at the reference sensor can compromise the signal to noise ratio which consequently perturbs their ability to obtain stable glucose readings in this environment. The sensors of the invention therefore overcome the difficulties observed with such oxygen sensors in non-vascular regions.

In some embodiments of the invention, the analyte sensor apparatus is designed to function via anodic polarization such that the alteration in current is detected at the anodic working electrode in the conductive layer of the analyte sensor apparatus. Structural design features that can be associated with anodic polarization include designing an appropriate sensor configuration comprising a working electrode which is an anode, a counter electrode which is a cathode and a reference electrode, and then selectively disposing the appropriate analyte sensing layer on the appropriate portion of the surface of the anode within this design configuration. Optionally this anodic polarization structural design includes anodes, cathodes and/or working electrodes having different sized surface areas. For example, this structural design includes features where the working electrode (anode) and/or the coated surface of the working electrode is larger or smaller than the counter electrode (cathode) and/or the coated surface of the counter electrode (e.g. a sensor designed to have a 1× area for a reference electrode, a 2.6× area for a working electrode and a 3.6× area for a counter electrode). In this context, the alteration in current that can be detected at the anodic working electrode is then correlated with the concentration of the analyte. In certain illustrative examples of this embodiment of the invention, the working electrode is measuring and utilizing hydrogen peroxide in the oxidation reaction (see e.g. FIG. 1), hydrogen peroxide that is produced by an enzyme such as glucose oxidase or lactate oxidase upon reaction with glucose or lactate respectively.

II. Illustrative Methods and Materials for Making Analyte Sensor Apparatus of the Invention A number of articles, U.S. patents and patent application describe the state of the art with the common methods and materials disclosed herein and further describe various elements (and methods for their manufacture) that can be used in the sensor designs disclosed herein. These include for example, U.S. Pat. Nos. 6,413,393; 6,368,274; 5,786,439; 5,777,060; 5,391,250; 5,390,671; 5,165,407, 4,890,620, 5,390,671, 5,390,691, 5,391,250, 5,482,473, 5,299,571, 5,568,806; United States Patent Application 20020090738; as well as PCT International Publication Numbers WO 01/58348, WO 03/034902, WO 03/035117, WO 03/035891, WO 03/023388, WO 03/022128, WO 03/022352, WO 03/023708, WO 03/036255, WO03/036310 and WO 03/074107, the contents of each of which are incorporated herein by reference.

Typical sensors for monitoring glucose concentration of diabetics are further described in Shichiri, et al.: "In Vivo Characteristics of Needle-Type Glucose Sensor-Measurements of Subcutaneous Glucose Concentrations in Human Volunteers," Horm. Metab. Res., Suppl. Ser. 20:17-20 (1988); Bruckel, et al.: "In Vivo Measurement of Subcutaneous Glucose Concentrations with an Enzymatic Glucose Sensor and a Wick Method," Klin. Wochenschr. 67:491-495 (1989); and Pickup, et al.: "In Vivo Molecular Sensing in Diabetes Mellitus: An Implantable Glucose Sensor with Direct Electron Transfer," Diabetologia 32:213-217 (1989). Other sensors are described in, for example Reach, et al., in ADVANCES IN IMPLANTABLE DEVICES, A. Turner (ed.), JAI Press, London, Chap. 1, (1993), incorporated herein by reference.

A. General Methods for Making Analyte Sensors

A typical embodiment of the invention disclosed herein is a method of making a sensor apparatus for implantation within a mammal comprising the steps of: providing a base layer; forming a conductive layer on the base layer, wherein the conductive layer includes an electrode (and typically a working electrode, a reference electrode and a counter electrode); forming a interference rejection membrane on the conductive layer, forming an analyte sensing layer on the interference rejection membrane, wherein the analyte sensing layer includes a composition that can alter the electrical current at the electrode in the conductive layer in the presence of an analyte; optionally forming a protein layer on the analyte sensing layer; forming an adhesion promoting layer on the analyte sensing layer or the optional protein layer; forming an analyte modulating layer disposed on the adhesion promoting layer, wherein the analyte modulating layer includes a composition that modulates the diffusion of the analyte therethrough; and forming a cover layer disposed on at least a portion of the analyte modulating layer, wherein the cover layer further includes an aperture over at least a portion of the analyte modulating layer. In certain embodiments of the invention, the analyte modulating layer comprises a hydrophilic comb-copolymer having a central chain and a plurality of side chains coupled to the central chain, wherein at least one side chain comprises a silicone moiety. In some embodiments of these methods, the analyte sensor apparatus is formed in a planar geometric configuration As disclosed herein, the various layers of the sensor can be manufactured to exhibit a variety of different characteristics which can be manipulated according to the specific design of the sensor. For example, the adhesion promoting layer includes a compound selected for its ability to stabilize the overall sensor structure, typically a silane composition. In some embodiments of the invention, the analyte sensing layer is formed by a spin coating process and is of a thickness selected from the group consisting of less than 1, 0.5, 0.25 and 0.1 microns in height.

Typically, a method of making the sensor includes the step of forming a protein layer on the analyte sensing layer, wherein a protein within the protein layer is an albumin selected from the group consisting of bovine serum albumin and human serum albumin. Typically, a method of making the sensor includes the step of forming an analyte sensing layer that comprises an enzyme composition selected from the group consisting of glucose oxidase, glucose dehydrogenase, lactate oxidase, hexokinase and lactate dehydrogenase. In such methods, the analyte sensing layer typically comprises a carrier protein composition in a substantially fixed ratio with the enzyme, and the enzyme and the carrier protein are distributed in a substantially uniform manner throughout the analyte sensing layer.

B. Typical Protocols and Materials Useful in the Manufacture of Analyte Sensors

The disclosure provided herein includes sensors and sensor designs that can be generated using combinations of various well known techniques. The disclosure further provides methods for applying very thin enzyme coatings to these types of sensors as well as sensors produced by such processes. In this context, some embodiments of the invention include methods for making such sensors on a substrate according to art accepted processes. In certain embodiments, the substrate comprises a rigid and flat structure suitable for use in photolithographic mask and etch processes. In this regard, the substrate typically defines an upper surface having a high degree of uniform flatness. A polished glass plate may be used to define the smooth upper surface.

Alternative substrate materials include, for example, stainless steel, aluminum, and plastic materials such as delrin, etc. In other embodiments, the substrate is non-rigid and can be another layer of film or insulation that is used as a substrate, for example plastics such as polyimides and the like.

An initial step in the methods of the invention typically includes the formation of a base layer of the sensor. The base layer can be disposed on the substrate by any desired means, for example by controlled spin coating. In addition, an adhesive may be used if there is not sufficient adhesion between the substrate layer and the base layer. A base layer of insulative material is formed on the substrate, typically by applying the base layer material onto the substrate in liquid form and thereafter spinning the substrate to yield the base layer of thin, substantially uniform thickness. These steps are repeated to build up the base layer of sufficient thickness, followed by a sequence of photolithographic and/or chemical mask and etch steps to form the conductors discussed below. In an illustrative form, the base layer comprises a thin film sheet of insulative material, such as ceramic or polyimide substrate. The base layer can comprise an alumina substrate, a polyimide substrate, a glass sheet, controlled pore glass, or a planarized plastic liquid crystal polymer. The base layer may be derived from any material containing one or more of a variety of elements including, but not limited to, carbon, nitrogen, oxygen, silicon, sapphire, diamond, aluminum, copper, gallium, arsenic, lanthanum, neodymium, strontium, titanium, yttrium, or combinations thereof. Additionally, the substrate may be coated onto a solid support by a variety of methods well-known in the art including physical vapor deposition, or spin-coating with materials such as spin glasses, chalcogenides, graphite, silicon dioxide, organic synthetic polymers, and the like.

The methods of the invention further include the generation of a conductive layer having one or more sensing elements. Typically these sensing elements are electrodes that are formed by one of the variety of methods known in the art such as photoresist, etching and rinsing to define the geometry of the active electrodes. The electrodes can then be made electrochemically active, for example by electrodeposition of Pt black for the working and counter electrode, and silver followed by silver chloride on the reference electrode. A sensor layer such as a analyte sensing enzyme layer can then be disposed on the sensing layer by electrochemical deposition or a method other than electrochemical deposition such a spin coating, followed by vapor crosslinking, for example with a dialdehyde (glutaraldehyde) or a carbodiimide.

Electrodes of the invention can be formed from a wide variety of materials known in the art. For example, the electrode may be made of a noble late transition metals. Metals such as gold, platinum, silver, rhodium, iridium, ruthenium, palladium, or osmium can be suitable in various embodiments of the invention. Other compositions such as carbon or mercury can also be useful in certain sensor embodiments. Of these metals, silver, gold, or platinum is typically used as a reference electrode metal. A silver electrode which is subsequently chloridized is typically used as the reference electrode. These metals can be deposited by any means known in the art, including the plasma deposition method cited, supra, or by an electroless method which may involve the deposition of a metal onto a previously metallized region when the substrate is dipped into a solution containing a metal salt and a reducing agent. The electroless method proceeds as the reducing agent donates electrons to the conductive (metallized) surface with the concomitant reduction of the metal salt at the conductive surface. The result is a layer of adsorbed metal. (For additional discussions on electroless methods, see: Wise, E. M. Palladium: Recovery, Properties, and Uses, Academic Press, New York, New York (1988); Wong, K. et al. Plating and Surface Finishing 1988, 75, 70-76; Matsuoka, M. et al. Ibid. 1988, 75, 102-106; and Pearlstein, F. "Electroless Plating," Modern Electroplating, Lowenheim, F. A., Ed., Wiley, New York, N.Y. (1974), Chapter 31). Such a metal deposition process must yield a structure with good metal to metal adhesion and minimal surface contamination, however, to provide a catalytic metal electrode surface with a high density of active sites. Such a high density of active sites is a property necessary for the efficient redox conversion of an electro-active species such as hydrogen peroxide.

In an exemplary embodiment of the invention, the base layer is initially coated with a thin film conductive layer by electrode deposition, surface sputtering, or other suitable process step. In one embodiment this conductive layer may be provided as a plurality of thin film conductive layers, such as an initial chrome-based layer suitable for chemical adhesion to a polyimide base layer followed by subsequent formation of thin film gold-based and chrome-based layers in sequence. In alternative embodiments, other electrode layer conformations or materials can be used. The conductive layer is then covered, in accordance with conventional photolithographic techniques, with a selected photoresist coating, and a contact mask can be applied over the photoresist coating for suitable photoimaging. The contact mask typically includes one or more conductor trace patterns for appropriate exposure of the photoresist coating, followed by an etch step resulting in a plurality of conductive sensor traces remaining on the base layer. In an illustrative sensor construction designed for use as a subcutaneous glucose sensor, each sensor trace can include three parallel sensor elements corresponding with three separate electrodes such as a working electrode, a counter electrode and a reference electrode.

Portions of the conductive sensor layers are typically covered by an insulative cover layer, typically of a material such as a silicon polymer and/or a polyimide. The insulative cover layer can be applied in any desired manner. In an exemplary procedure, the insulative cover layer is applied in a liquid layer over the sensor traces, after which the substrate is spun to distribute the liquid material as a thin film overlying the sensor traces and extending beyond the marginal edges of the sensor traces in sealed contact with the base layer. This liquid material can then be subjected to one or more suitable radiation and/or chemical and/or heat curing steps as are known in the art. In alternative embodiments, the liquid material can be applied using spray techniques or any other desired means of application. Various insulative layer materials may be used such as photo-imagable epoxyacrylate, with an illustrative material comprising a photoimagable polyimide available from OCG, Inc. of West Paterson, N.J., under the product number 7020.

Embodiments of the invention can include forming an interference rejection layer on the conductive layer. For example, one can form an interference rejection membrane using 5 wt % poly(vinyl alcohol) crosslinked with 10-20 wt % crosslinker for a spray application process (which can, for example, be determined via the dispensing method). In certain embodiments of the invention, the PVA includes silanol functional group, such as the Kurarray R-polymer R1130, which produce highly desirable interference rejection effects. In specific embodiments, one can form an interference rejection membrane using 5 wt % poly(vinyl alcohol) crosslinked with 10 wt % sulfosuccinic acid. Such processes can include a heating/curing step. In typical embodiments, the heating temperature for curing the membrane can range from 130° C.-150° C. for at least 40 minutes (e.g. 40-60 minutes). A wide variety of permutations of such methods will be apparent to artisans. In one illustrative embodiment, one can apply the interference rejection membrane by spin coating at 400-1200 rpm and curing at a temperature between 130° C.-150° C. In a specific instance, artisans can apply the interference rejection membrane by spin coating at 400-500 rpm and curing at a temperature of 130° C. for at least 40 minutes (e.g. 40-60 minutes).

In certain embodiments of the invention materials used to form one or more layers of a sensor stack are selected to control their diffusion coefficients for one or more compounds such as $O_2$ or glucose. Typically, for example, materials forming the interference rejection membrane and/or materials forming the analyte modulating layer are selected so that the diffusivity of $O_2$ diffusion coefficient through said layers is at least $1.0\times10^{-5}$ cm$^2$/s 37° C. in phosphate buffered saline (e.g. is between 1.0 and $3.0\times10^{-5}$ cm$^2$/s 37° C.). Similarly, in illustrative embodiments of the invention, the materials forming the interference rejection membrane and/or materials forming the analyte modulating layer are selected so as to exhibit a glucose permeability of at least $1\times10^{-8}$ cm$^2$/s at 37° C. in phosphate buffered saline.

In an illustrative sensor embodiment for use as a glucose sensor, an enzyme (typically glucose oxidase) is coated with the enzyme so as to define a working electrode. One or both of the other electrodes can be provided with the same coating as the working electrode. Alternatively, the other two electrodes can be provided with other suitable chemistries, such as other enzymes, left uncoated, or provided with chemistries to define a reference electrode and a counter electrode for the electrochemical sensor. Methods for producing the enzyme coatings include spin coating processes, dip and dry processes, low shear spraying processes, ink-jet printing processes, silk screen processes and the like. Typically, such coatings are vapor crosslinked subsequent to their application. Surprisingly, sensors produced by these processes have material properties that exceed those of sensors having coatings produced by electrodeposition including enhanced longevity, linearity, regularity as well as improved signal to noise ratios. In addition, embodiments of the invention that utilize glucose oxidase coatings formed by such processes are designed to recycle hydrogen peroxide and improve the biocompatibility profiles of such sensors.

Sensors generated by processes such as spin coating processes also avoid other problems associated with electrodeposition, such as those pertaining to the material stresses placed on the sensor during the electrodeposition process. In particular, the process of electrodeposition is observed to produce mechanical stresses on the sensor, for example mechanical stresses that result from tensile and/or compression forces. In certain contexts, such mechanical stresses may result in sensors having coatings with some tendency to crack or delaminate. This is not observed in coatings disposed on sensor via spin coating or other low-stress processes.

In some embodiments of the invention, the sensor is made by methods which apply an analyte modulating layer that comprises a hydrophilic membrane coating which can regulate the amount of analyte that can access the enzyme of the sensor layer. For example, the cover layer that is added to the glucose sensors of the invention can comprise a glucose limiting membrane, which regulates the amount of glucose that access glucose oxidase enzyme layer on an electrode.

Such glucose limiting membranes can be made from a wide variety of materials known to be suitable for such purposes, e.g., silicones such as polydimethyl siloxane and the like, polyurethanes, cellulose acetates, NAFION, polyester sulfonic acids (e.g. Kodak AQ), hydrogels or any other membrane known to those skilled in the art that is suitable for such purposes. In certain embodiments of the invention, the analyte modulating layer comprises a hydrophilic comb-copolymer having a central chain and a plurality of side chains coupled to the central chain, wherein at least one side chain comprises a silicone moiety. In some embodiments of the invention pertaining to sensors having hydrogen peroxide recycling capabilities, the membrane layer that is disposed on the glucose oxidase enzyme layer functions to inhibit the release of hydrogen peroxide into the environment in which the sensor is placed and to facilitate hydrogen peroxide molecules and accessing the electrode sensing elements.

In some embodiments of the methods of invention, an adhesion promoter layer is disposed between a cover layer (e.g. an analyte modulating membrane layer) and a analyte sensing layer in order to facilitate their contact and is selected for its ability to increase the stability of the sensor apparatus. As noted herein, compositions of the adhesion promoter layer are selected to provide a number of desirable characteristics in addition to an ability to provide sensor stability. For example, some compositions for use in the adhesion promoter layer are selected to play a role in interference rejection as well as to control mass transfer of the desired analyte. The adhesion promoter layer can be made from any one of a wide variety of materials known in the art to facilitate the bonding between such layers and can be applied by any one of a wide variety of methods known in the art. Typically, the adhesion promoter layer comprises a silane compound such as $\gamma$-aminopropyltrimethoxysilane. In certain embodiments of the invention, the adhesion promoting layer and/or the analyte modulating layer comprises an agent selected for its ability to crosslink a siloxane moiety present in a proximal. In other embodiments of the invention, the adhesion promoting layer and/or the analyte modulating layer comprises an agent selected for its ability to crosslink an amine or carboxyl moiety of a protein present in a proximal layer. In an optional embodiment, the AP layer further comprises Polydimethyl Siloxane (PDMS), a polymer typically present in analyte modulating layers such as a glucose limiting membrane. In illustrative embodiments the formulation comprises 0.5-20% PDMS, typically 5-15% PDMS, and most typically 10% PDMS. The addition of PDMS to the AP layer can be advantageous in contexts where it diminishes the possibility of holes or gaps occurring in the AP layer as the sensor is manufactured.

One illustrative embodiment of the invention is a method of making a sensor electrode by providing an electroactive surface which can function as an electrode (e.g. platinum), forming an interference rejection membrane on the electroactive surface, spin coating an enzyme layer on the IRM and then forming an analyte contacting layer (e.g. an analyte modulating layer such as a glucose limiting membrane) on the electrode, wherein the analyte contacting layer regulates the amount of analyte that can contact the enzyme layer. In some methods, the enzyme layer is vapor crosslinked on the sensor layer. In a typical embodiment of the invention, a sensor is formed to include at least one working electrode and at least one counter electrode. In certain embodiments, the IRM is formed on at least a portion of the working electrode and at least a portion of the counter electrode. Typically, the enzyme layer comprises one or more enzymes such as glucose oxidase, glucose dehydrogenase, lactate oxidase, hexokinase or lactate dehydrogenase and/or like enzymes. In a specific method, the enzyme layer comprises glucose oxidase that is stabilized by coating it on the sensor layer in combination with a carrier protein in a fixed ratio. Typically the carrier protein is albumin. Typically such methods include the step of forming an adhesion promoter layer disposed between the glucose oxidase layer and the analyte contacting layer. Optionally, a layer such as the IRM and/or the adhesion promoter layer is subjected to a curing process prior to the formation of the analyte contacting layer.

The finished sensors produced by such processes are typically quickly and easily removed from a supporting substrate (if one is used), for example, by cutting along a line surrounding each sensor on the substrate. The cutting step can use methods typically used in this art such as those that include a UV laser cutting device that is used to cut through the base and cover layers and the functional coating layers along a line surrounding or circumscribing each sensor, typically in at least slight outward spaced relation from the conductive elements so that the sufficient interconnected base and cover layer material remains to seal the side edges of the finished sensor. In addition, dicing techniques typically used to cut ceramic substrates can be used with the appropriate sensor embodiments. Since the base layer is typically not physically attached or only minimally adhered directly to the underlying supporting substrate, the sensors can be lifted quickly and easily from the supporting substrate, without significant further processing steps or potential damage due to stresses incurred by physically pulling or peeling attached sensors from the supporting substrate. The supporting substrate can thereafter be cleaned and reused, or otherwise discarded. The functional coating layer(s) can be applied either before or after other sensor components are removed from the supporting substrate (e.g., by cutting).

III. Methods for Using Analyte Sensor Apparatus of the Invention

Related embodiments of the invention is a method of sensing an analyte within the body of a mammal, the method comprising implanting an analyte sensor embodiment disclosed herein in to the mammal and then sensing one or more electrical fluctuations such as alteration in current at the working electrode and correlating the alteration in current with the presence of the analyte, so that the analyte is sensed. In one such method, the analyte sensor apparatus senses glucose in the mammal. In an alternative method, the analyte sensor apparatus senses lactate, potassium, calcium, oxygen, pH, and/or any physiologically relevant analyte in the mammal.

Certain analyte sensors having the structure discussed above have a number of highly desirable characteristics which allow for a variety of methods for sensing analytes in a mammal. For example in such methods, the analyte sensor apparatus implanted in the mammal functions to sense an analyte within the body of a mammal for more than 1, 2, 3, 4, 5, or 6 months. Typically, the analyte sensor apparatus so implanted in the mammal senses an alteration in current in response to an analyte within 15, 10, 5 or 2 minutes of the analyte contacting the sensor. In such methods, the sensors can be implanted into a variety of locations within the body of the mammal, for example in both vascular and non-vascular spaces.

IV. Kits and Sensor Sets of the Invention

In another embodiment of the invention, a kit and/or sensor set, useful for the sensing an analyte as is described above, is provided. The kit and/or sensor set typically comprises a container, a label and an analyte sensor as described above. Suitable containers include, for example, an easy to open package made from a material such as a metal foil, bottles, vials, syringes, and test tubes. The containers may be formed from a variety of materials such as metals (e.g. foils) paper products, glass or plastic. The label on, or associated with, the container indicates that the sensor is used for assaying the analyte of choice. In some embodiments, the container holds a porous matrix that is coated with a layer of an enzyme such as glucose oxidase. The kit and/or sensor set may further include other materials desirable from a commercial and user standpoint, including elements or devices designed to facilitate the introduction of the sensor into the analyte environment, other buffers, diluents, filters, needles, syringes, and package inserts with instructions for use.

EXAMPLES

Example 1: Mechanistic Principles and Associated Methods and Materials Useful for Practicing Embodiments of the Invention Eliminating sensor signal interference that results from small neutral compounds such as acetaminophen (Mw=151.17 Daltons) is challenging considering their typically smaller size than sensed analytes such as glucose (Mw=180.15 Daltons). While the use of polymer(s) thin films in sensors has been attempted in the art, eliminating interference remains problematical because of such film's insufficient density (even if using a very high molecular weight polymer). In order to keep sensor signals at a high level and quick start-up properties, membrane structures used for interference rejection should be extremely dense and hydrophilic.

As disclosed herein, a direct thin film coating followed by a crosslinking of hydrophilic polymer system is an ideal option when considering the requirements listed above.
IRMs Useful in Anayte Sensors In typical sensor designs, glucose reaches the enzyme glucose oxidase, where it is oxidized to gluconic acid by oxygen, leaving $H_2O_2$. One molecule of glucose gives one molecule of $H_2O_2$ at the expense of one molecule of oxygen:

$$C_6H_{12}O_6+H_2O_2 \rightarrow C_5H_{11}O_5COOH+H_2O_2 \qquad (1)$$

At the working electrode $H_2O_2$ is oxidized and the oxygen is regenerated:

$$H_2O_2 \rightarrow O_2+2H^++2e- \qquad (2)$$

It is seen that in case all the enzymatically generated $H_2O_2$ (Mw=34.02 Daltons). reaches the working electrode the oxygen is fully recovered.

At the counter electrode some reduction process occurs, the following 3 reactions are possible:

$$2H_2O+2e- \rightarrow H_2+2OH- \qquad (3)$$

$$H_2O_2+2e- \rightarrow 2OH- \qquad (4)$$

$$\frac{1}{2}O_2+2H^++2e- \rightarrow H_2O \qquad (5)$$

Reaction (3) will then proceed as the sensor is in an aqueous environment. Any of the three reactions on the counter electrode will serve to neutralize the protons generated in reaction (2), so the total increase in acidity is caused by the gluconic acid only. The net reaction as sensor functions produces gluconic acid and $H_2$ (at the expense of glucose and $H_2O$.

The present invention provides an interference rejection membrane (IRM) that retards diffusion of interfering, elec-troactive compounds such as acetaminophen and ascorbic acid relative to the diffusion of the $H_2O_2$ generated by the enzyme reaction, thereby inhibiting and/or eliminating the co-measurements of these interferents because interferent compounds can no longer reach the working electrode during the current measuring period (are inhibited from reaching the working electrode).

Another technical advantage to using sensors having the hydrophilic interference rejection membranes disclosed herein is a reduction of the start-up/initialization time, which is the time after the sensor's placement in vivo that it takes for the sensor to functionally acclimate to this in vivo environment so as to give meaningful readings. Without being bound by a specific scientific theory, it is believed that this is due to the fact that by disposing the IRM directly on the surface of the working electrode, this coverage of the working electrode surface area by the IRM functions to effectively lower the background current much faster than occurs in sensors made without an IRM. In view of this, the initial current overshooting time associated with certain sensor embodiments disappears.

In certain embodiments of the invention the IRM comprises a crosslinked poly(vinyl alcohol) (PVA) polymer. As noted above, such semi-permeable membranes function via size exclusion of interfering compounds (e.g. as a sort of molecular sieve). In certain embodiments of the invention, the IRM inhibits the ability of interferents with molecular weights above 140 Daltons to diffuse to the working electrode of an analyte sensor.

Typically, the poly(vinyl alcohol) (PVA) polymers are crosslinked by crosslinkers or crosslinking agents in order to generate a tightly connected polymer network. As described herein, sulfosuccinic acid (SSA) is a very efficient crosslinker suitable for use with PVA. Poly(methyl vinyl ether-alt-maleic acid) is another crosslinker suitable for use with PVA to form an integrated dense polymer network. Other suitable crosslinkers include, for example, maleic acid, citric acid, oxalic acid, fumaric acid, poly(acrylic acid), poly (acrylic acid-co-maleic acid) (PAM), succinic acid, and malonic acid.

An IRM solution can be applied via a various processes including but not limited to, spray processes, spin coating processes, dip and dry processes, low shear spraying processes, ink-jet printing processes, silk screen processes and the like. One method for IRM deposition comprises spray coating with a BioDot™ system. In one illustrative example, the solution is applied over a plate and spin coated at a speed of 400-1200 rpm (depending on the surface roughness), resulting in a membrane thickness from 0.3-2 μm. The membrane is then dried before putting into a 130° C. oven and baked for approximately 40 minutes. After baking, the plate is cooled to room temperature and rinsed with $H_2O$, followed by a rinse in bicarbonate buffer (pH 7.2-8.0) for 15 minutes and a final rinse again in $H_2O$ to remove all of the non-crosslinked SSA for good biocompatibility. Sensors comprising this IRM were then built following standard manufacturing protocols. Finished in vitro sensor performances were evaluated at PBS (phosphate buffered saline), BTS (buffer test system) and/or SITS (sensor in-vitro test system) levels.

A variety of permutations from IRM recipes are contemplated. For example, a number of small molecular weight and high boiling point chemicals which cannot chemically interact with the polymer matrix and are compatible with the membrane system have been added into IRM formulation in order to create some porosity after being released into water so as to expedite the start-up and enhance Isig level. Considering its hydroscopic character, glycerol can be added to the IRM formulation as a plasticizer to reduce cracks and expedite initial hydration and start-up. A hydrophilic polymer with a primary-amine group that can be entrapped in the IRM crosslinked matrix is desirable. Some other more hydroscopic polymer with a hydroxyl group such as hydroxypropyl cellulose can be added to expedite the initial start-up. A variety of other crosslinker(s) can also be used in embodiments of the invention. For example, poly(methyl vinyl ether-alt-maleic acid) has been used as a crosslinker for PVA matrix. Different baking temperature and times have also been used to create IRMs having tailored properties. Other compounds such as hydrophilic polymers with hydroxy or primary amine groups can also be added into IRM formulations in order to make them more hydrophilic.

In one illustrative embodiment, the IRM solution is coated onto the sensor plate after the electrode plating process and before the enzyme process. If the IRM layer were to be placed above the enzyme layer, glucose could be prevented from diffuse through the IRM due to its molecular size. A second parameter for the IRM process characterization is the number of layers of IRM. After each layer of IRM is deposited, the membrane is crosslinked through a baking cycle of 130° C.-150° C.

In summary, PVA gives a competitive performance as compared to known IRM materials. High molecular weight or very high molecular weight polymer with appropriate crosslinking capability provides functional IRM that can be disposed on a rough Pt working electrode surface. In addition, PVA is compatible with the protein and GOx layers typically used in sensors. Consequently, there should be less of a possibility of cracking or delamination issues with sensors that employ such IRMs.

Example 2: PVA Sensor Performances

Figure 5A:
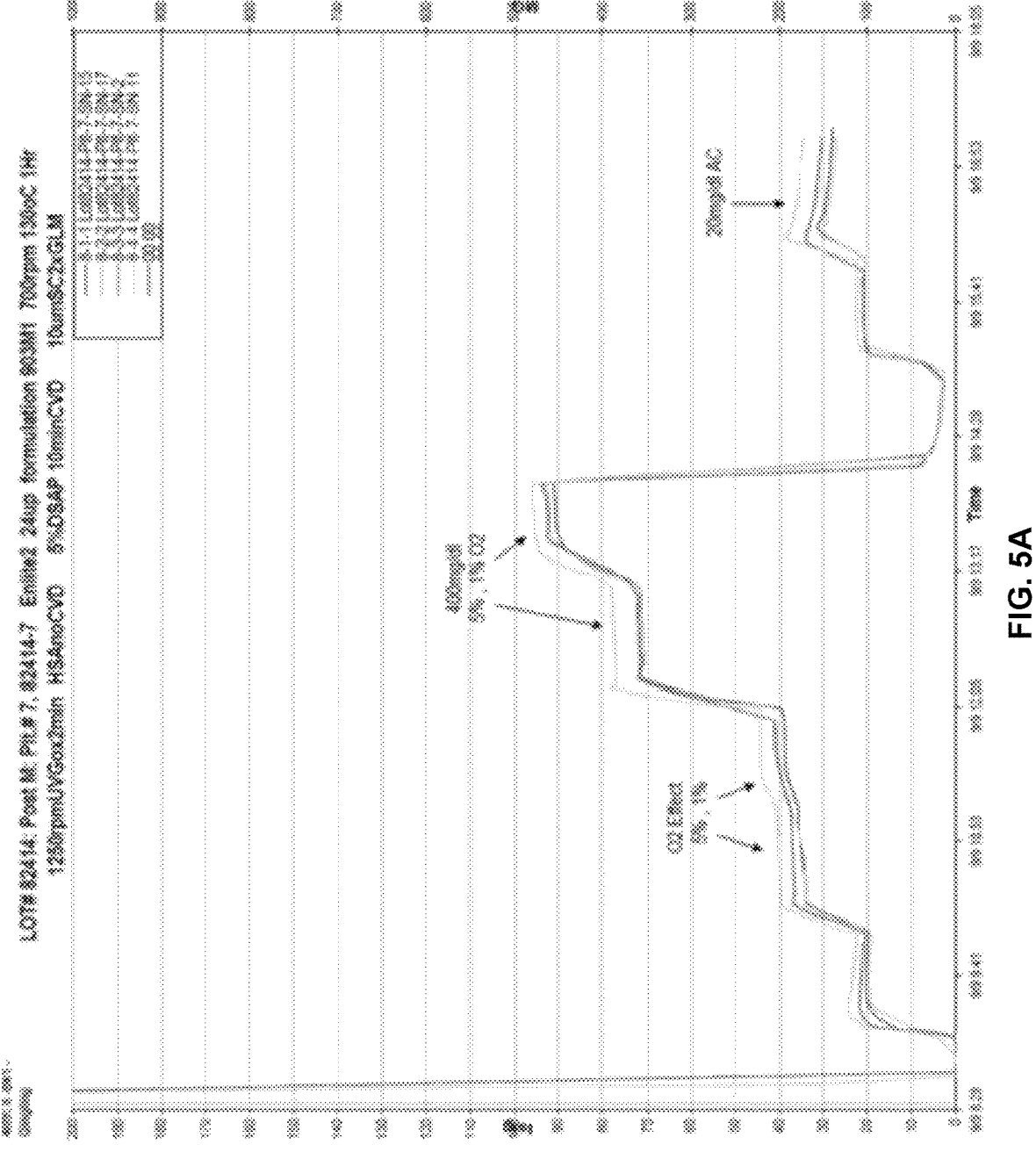
FIG. 5A provides graphs illustrating the in vitro performance of sensors, depicting buffer test system (BTS) results with (right panel) or without (left panel) an interference rejecting membranes (IRM).
Figure 5B:
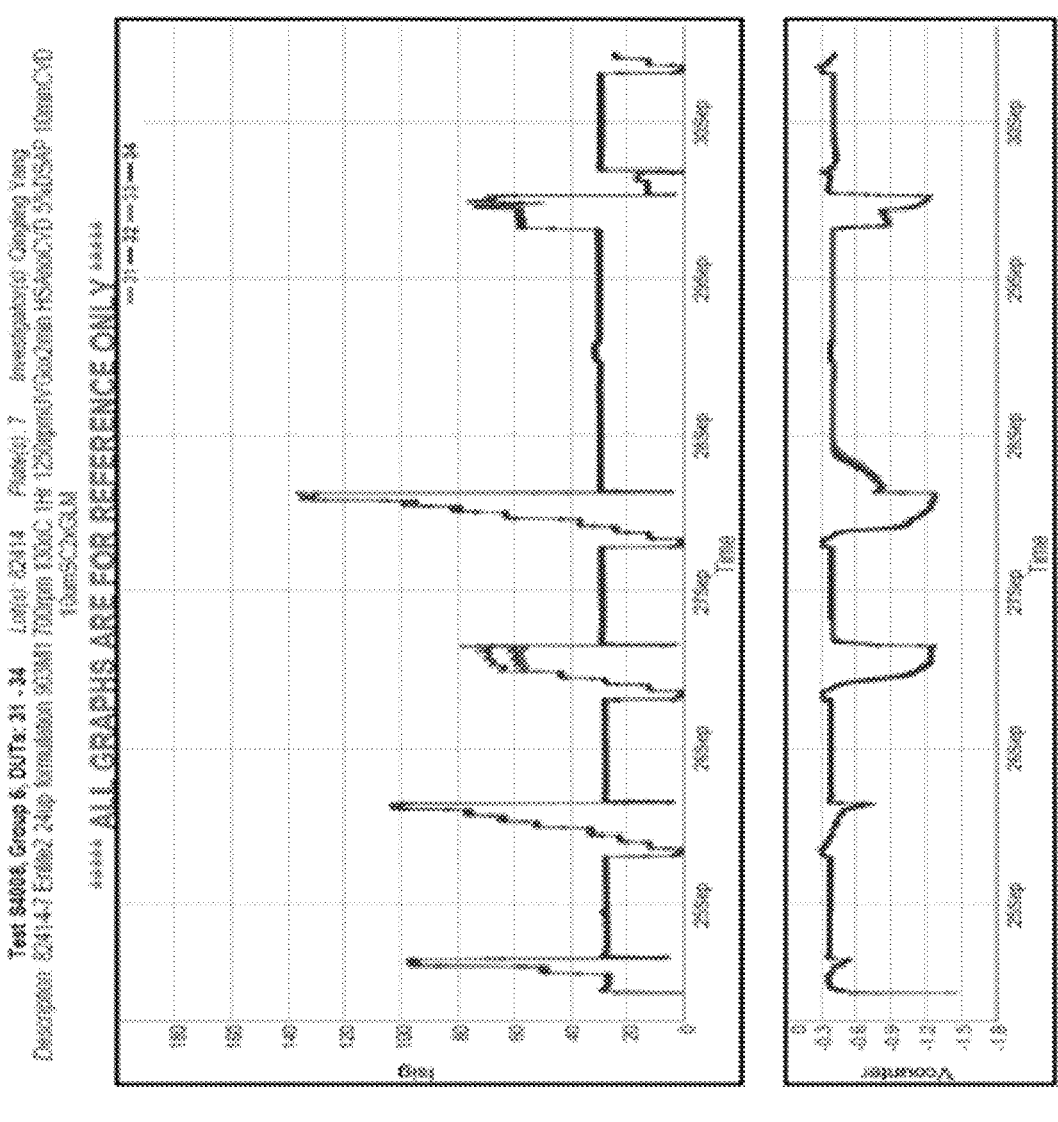
FIG. 5B provides graphs illustrating the in vitro performance of sensors, depicting sensor in vitro test system (SITS) results showing how one can modulate the $O_2$ effect using differing glucose limiting membrane (GLM) formulations.
Figure 5C:
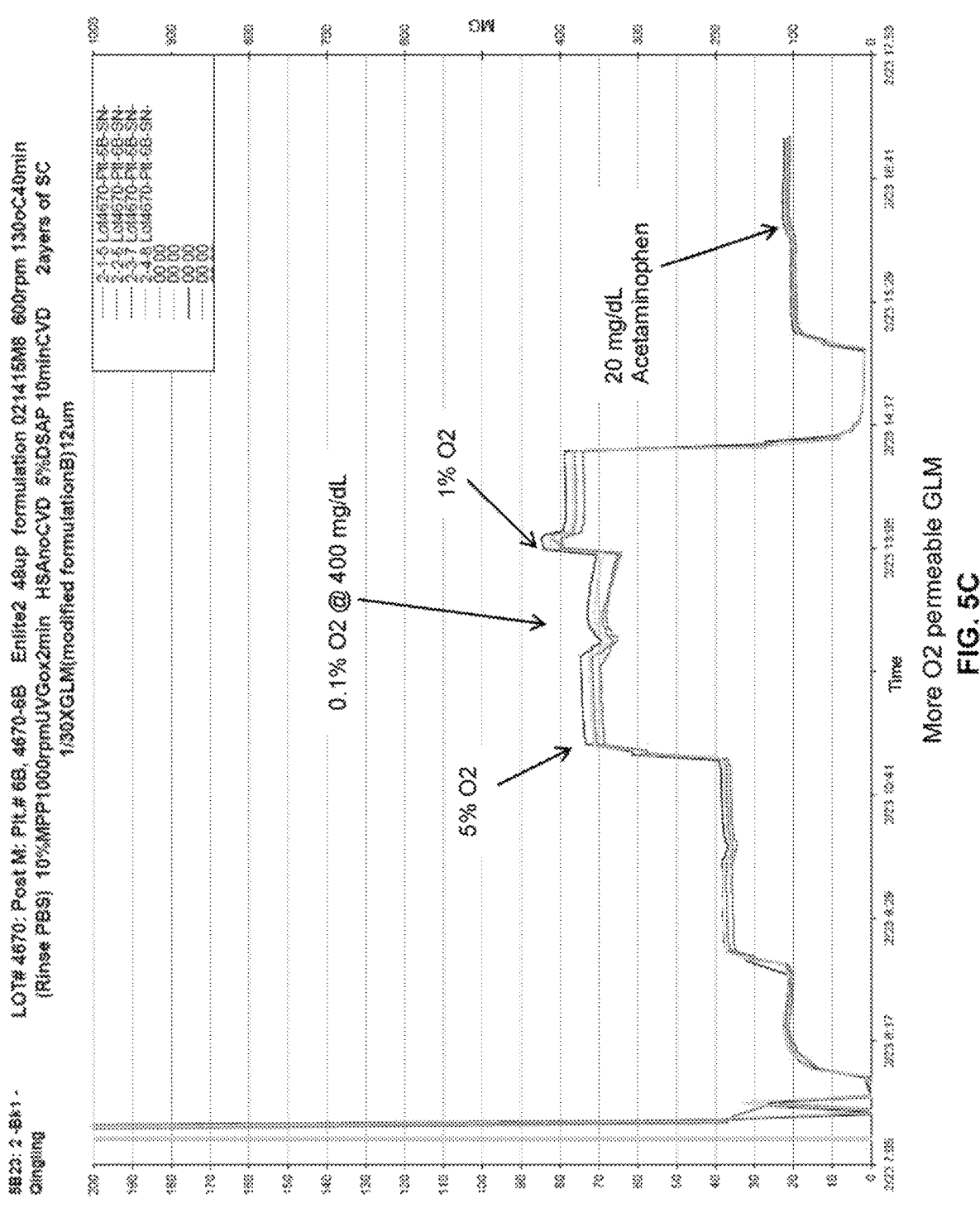
FIGS. 5C and 5D provides graphs illustrating the improved in vitro performance of sensors interference rejecting membranes (IRM) of the invention and different glucose limiting membrane compositions. These graphs of data in FIGS. 5C and 5D show that interference rejecting membranes of the invention exhibit a lower $O_2$ effect, a property that results in increased sensor accuracy.
Figure 5D:
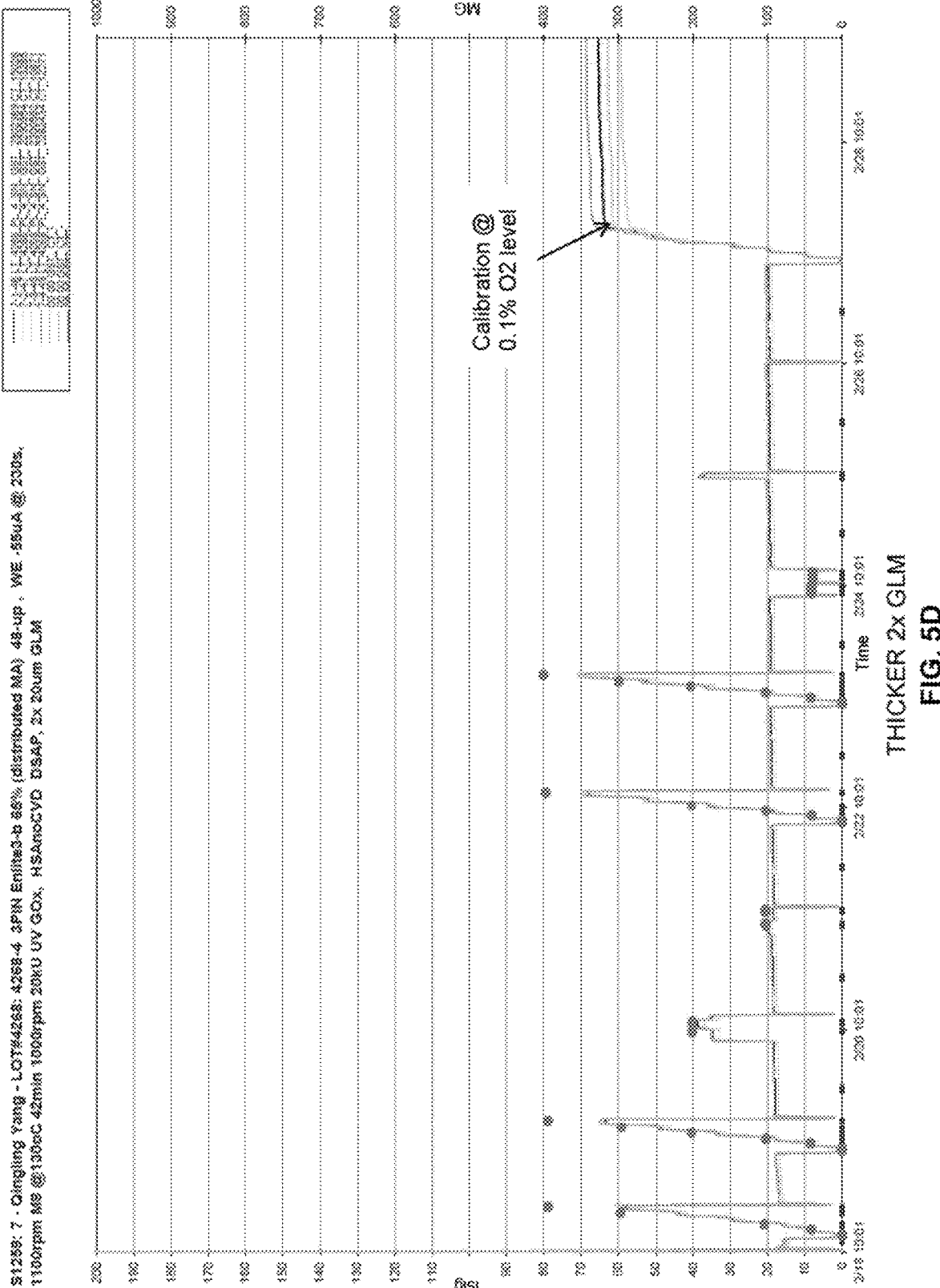

FIG. 5A provides graphs illustrating the in vitro performance of sensors, depicting buffer test system (BTS) results with (right panel) or without (left panel) an interference rejecting membranes (IRM). FIG. 5B provides graphs illustrating the in vitro performance of sensors, depicting sensor in vitro test system (SITS) results showing how one can modulate the $O_2$ effect using differing glucose limiting membrane (GLM) formulations. These graphs of data in FIGS. 5C and 5D show that interference rejecting membranes of the invention exhibit a lower $O_2$ effect, a property that results in increased sensor accuracy.

Figure 6:
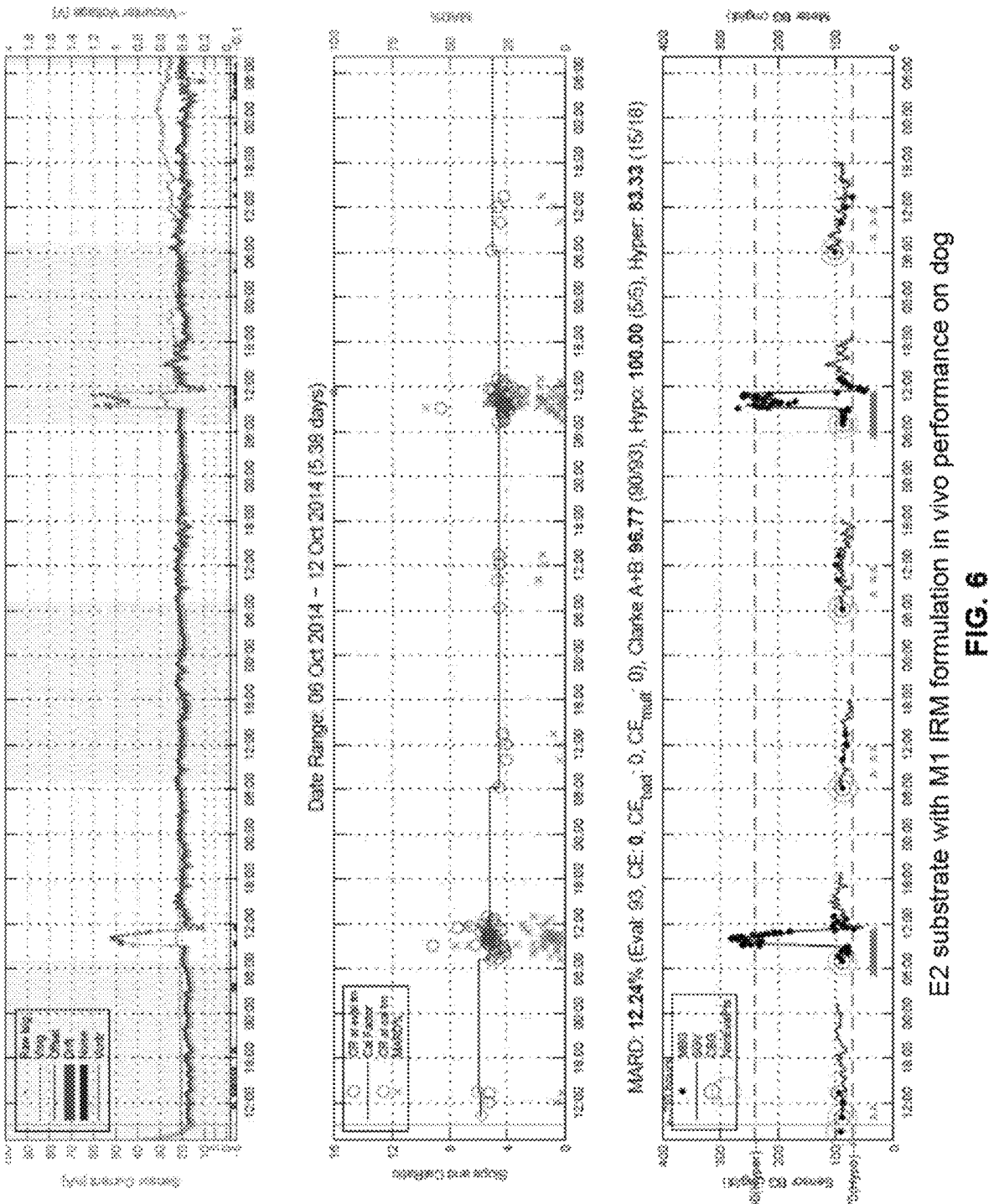
FIG. 6 provides graphs illustrating the in vivo performance of sensors on dogs, based on an E2 substrate with an IRM comprising an M1 formulation, in accordance with one or more embodiments of the invention.
Figure 7:
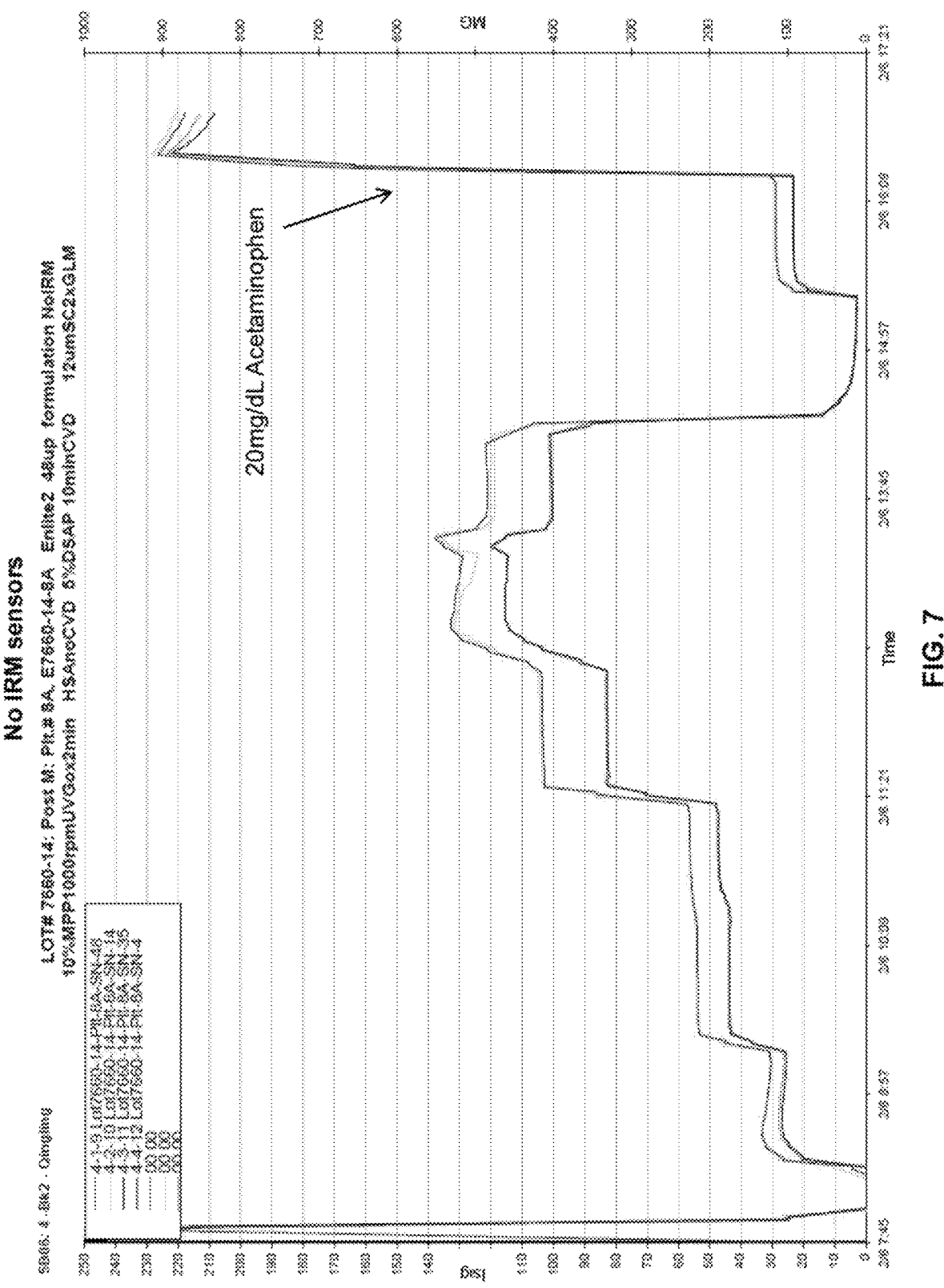
FIG. 7 provides a graph illustrating the Isig levels of sensors with no IRM and the effect when 20 mg/dL acetaminophen is introduced.
Figure 8:
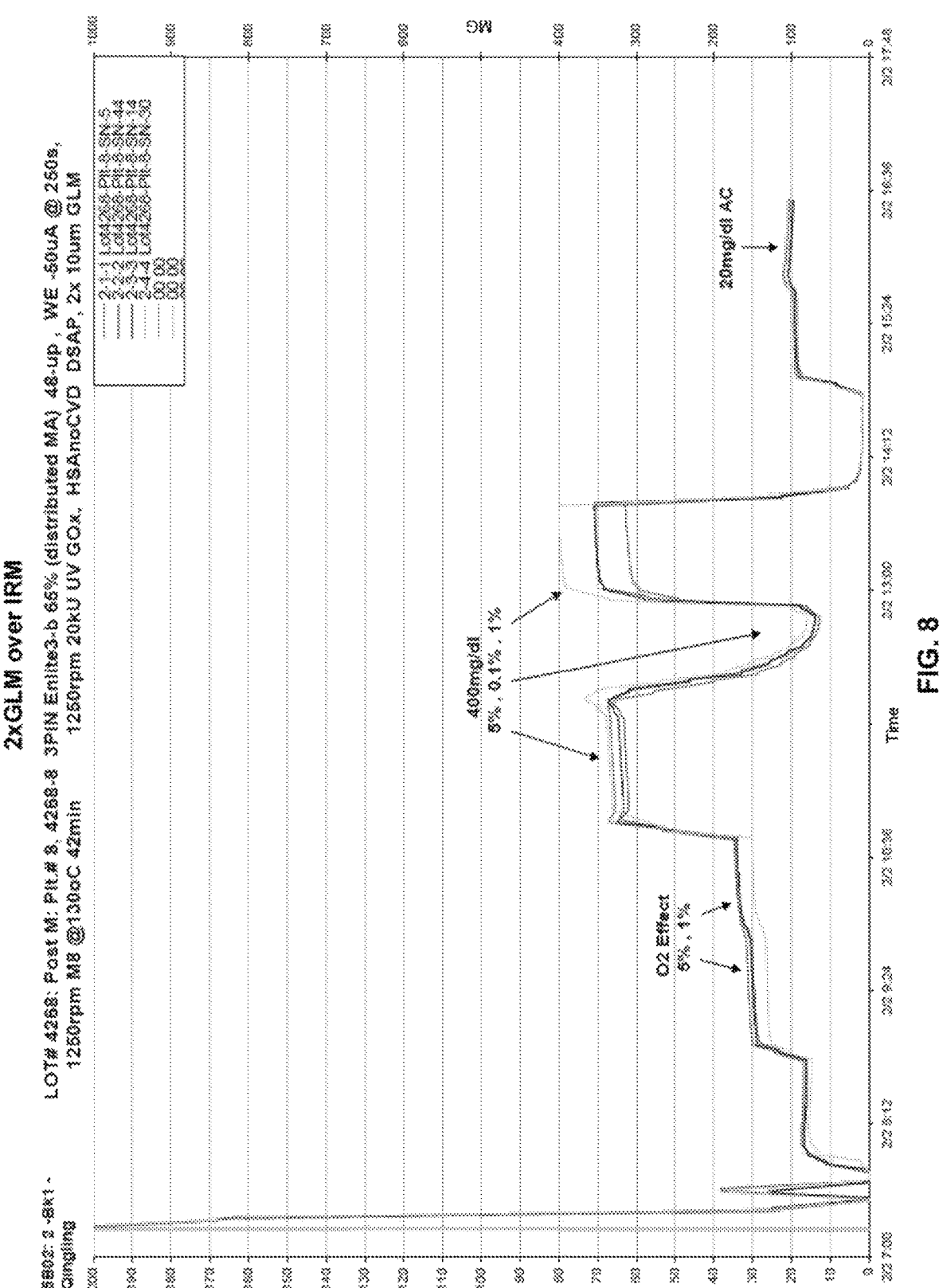
FIG. 8 provides a graph illustrating the Isig levels of sensors with 2× glucose limiting membrane (GLM) over an IRM, in accordance with one or more embodiments of the invention.
Figure 9:
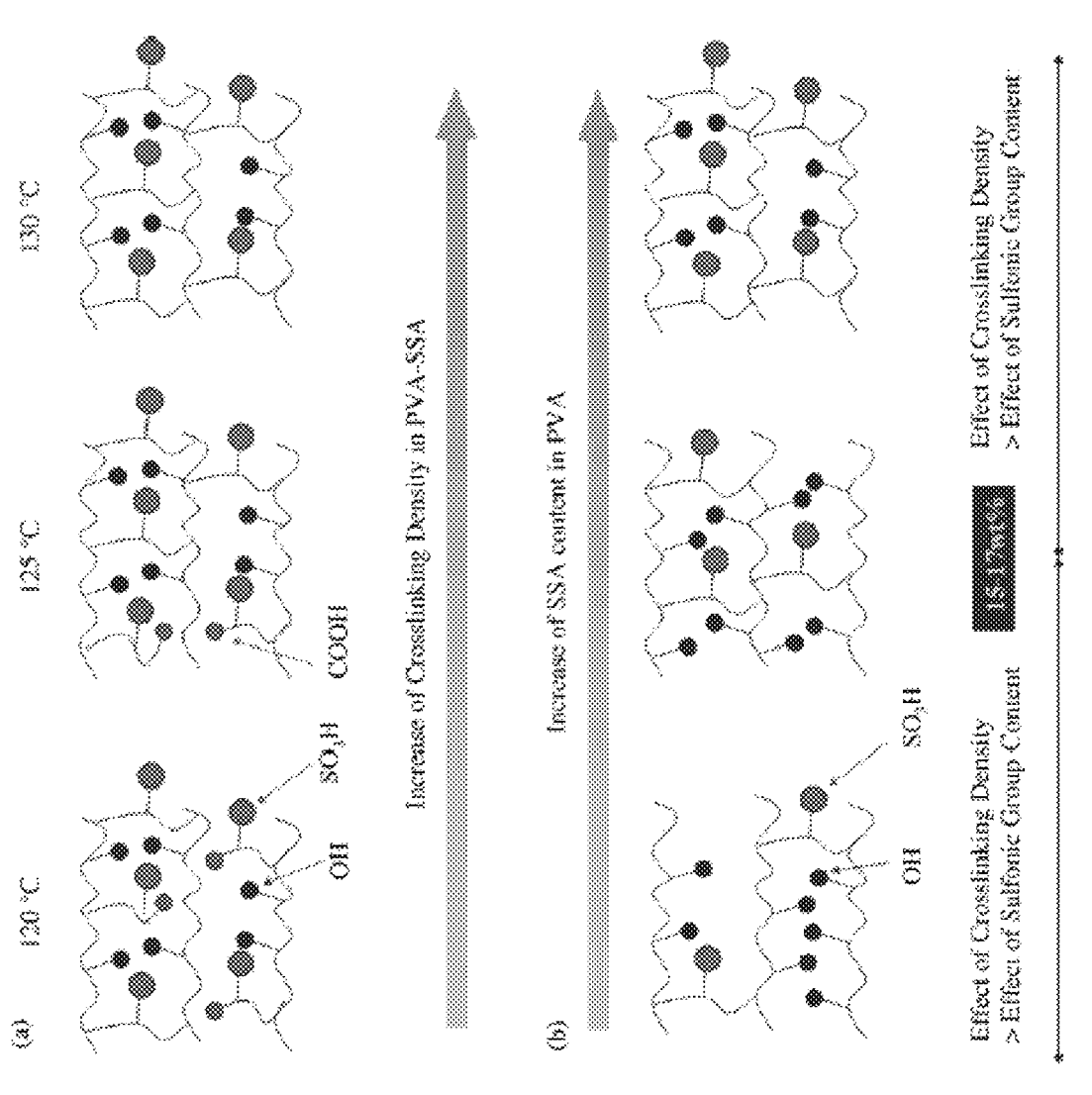
FIG. 9 provides illustrations of possible crosslinking mechanism of PVA/SSA: (a) the effect of crosslinking temperature and (b) the effect of the amount of SSA in the PVA matrix, in accordance with one or more embodiments of the invention.
Figure 10:
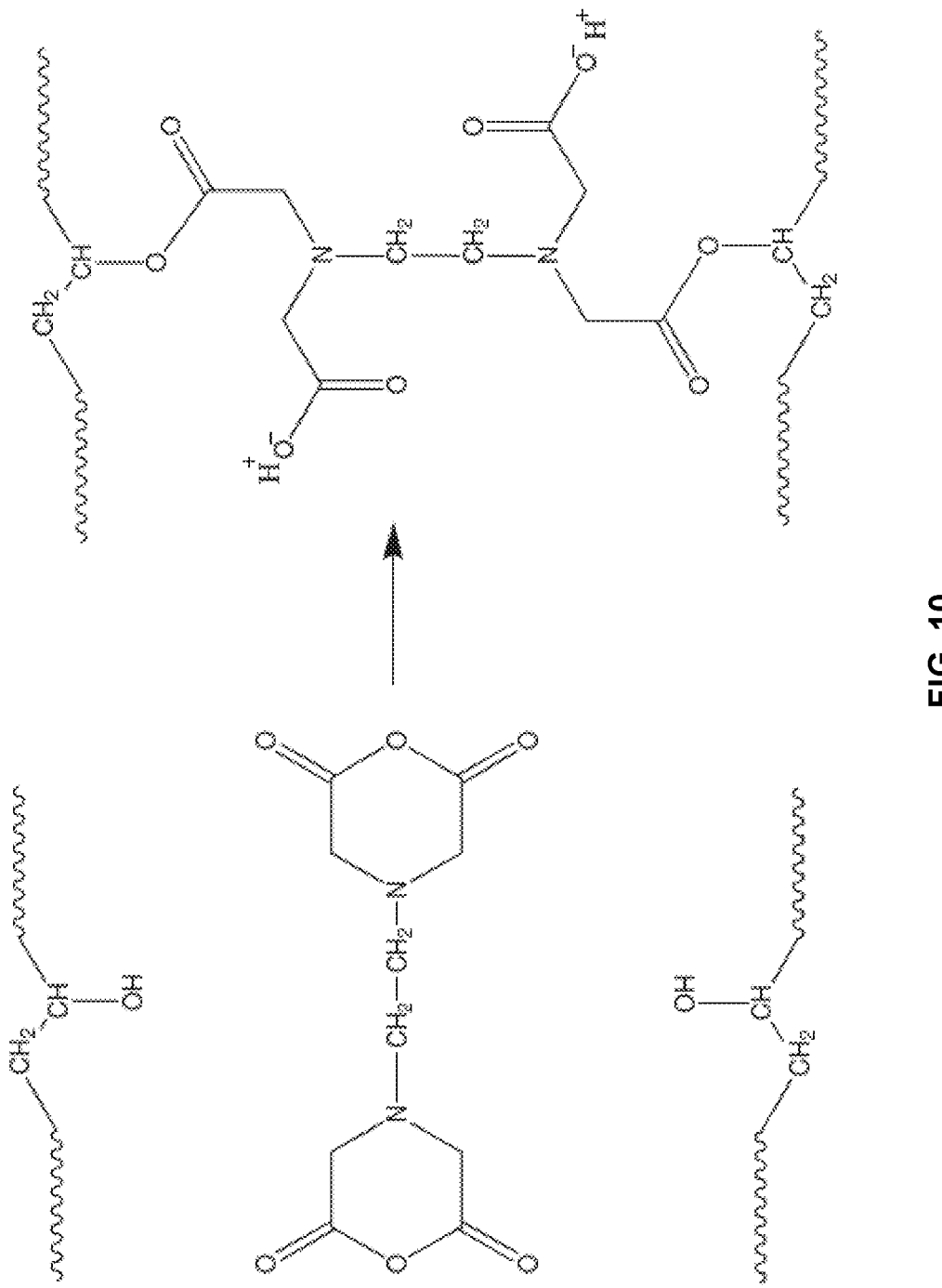
FIG. 10 provides an illustration of the crosslinking of poly(vinyl alcohol) (PVA) by ethylenediaminetetraacetic dianhydride (EDTAD), resulting in the formation of two carboxylic acids per crosslink site, in accordance with one or more embodiments of the invention.
Figure 13:
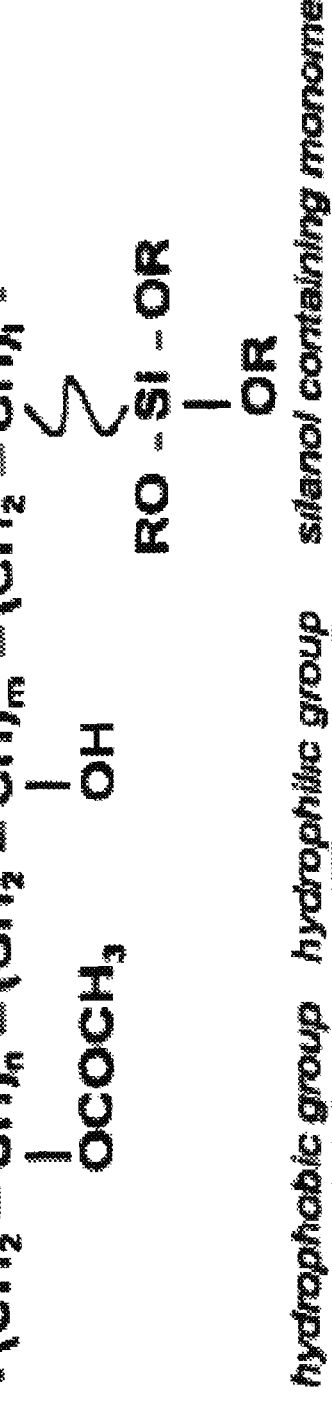
FIG. 13 provides an illustration of the molecular structure of a Kuraray "R-polymer".

FIG. 6 depicts in vivo sensor performance results on a canine model based on the E2 substrate with M1 IRM formulation. These results show that this group has good interference rejection characteristics and fine $O_2$ effect even under a 0.1% $O_2$ tension test. These results also demonstrate impressive in vivo performance. Isig level is consistent with BTS result and very stable through all of the 5 day test period. Vcounter is also quite stable.

Among all of the crosslinkers tested, sulfosuccinic acid SSA and poly(methyl vinyl ether-alt-maleic acid) were found to be the most efficient ones. Content of SSA ranged from 5-30% of PVA polymer weight. Extra cross linkers have to be removed from the membrane matrix post crosslinking reaction to ensure the biocompatibility and consistent Isig.

This example demonstrates that the IRM membrane based on PVA crosslinking polymer chemistry provided much fast start-up, easy process, better process capability and room for optimization of $O_2$ effect compared to other IRM (for example silane-pHEMA IRM). The IRM provided herein is also compatible with current UV GOx membrane systems.

Example 3: PVA-SSA Formulation M8

This example describes one embodiment of the invention, M8 IRM formulation. Formulation M8 comprises 5 g PVA (Kurrary™ R1130) aqueous solution (5%) with 0.8 mL SSA solution (10%, diluted from a stock solution of Sigma-Aldrich™). The solution was applied over a plate and spin coated at a speed of 400-1200 rpm (which depends on the surface roughness), resulting in a membrane thickness from 0.3-2 μm. Optimal membrane thickness is 0.4-0.8 μm. The membrane was dried before putting into a 130° C. oven and baked for 42 minutes. After baking, plates were cooled to room temperature and rinsed with $H_2O$, followed by a rinse in bicarbonate buffer (pH 7.2-8.0) for 15 minutes and a final rinse again in $H_2O$ to remove all of the non-crosslinked SSA for good biocompatibility. This silanol functional PVA has a high molecular weight (Mw).

Other commonly used nonfunctional PVAs can still be used as IRM, however the interference rejection efficiency or consistency is found to not be as good as this silanol functional PVA. This may be due to additional crosslinking between the silanol group and the —OH group on PVA. Common PVAs can be chosen from higher Mw ones ranging from 50 kD to 200 kD and with hydrolysis levels ranging from 88% to greater than 99%.

Example 4: PVA Crosslinked with PAA

In this example, poly(vinyl alcohol) (PVA) is crosslinked by esterification using poly(acrylic acid) (PAA) as a crosslinking reagent, resulting in a highly insoluble PVA material (see, e.g. J Appl Polym Sci 90: 2420-2427, 2003). Blend films of PVA and PAA (PVA/PAA=8/2 ratio) were prepared to examine the effect of degree of neutralization (DN) in PAA and heat-treatment conditions on the degree of crosslinking reaction. The degree of crosslinking reaction varied significantly when the DN of PAA changed. The optimum DN for the crosslinking reaction was in the range of 5 to 10 mol %. In the case of unneutralized PAA, the degree of crosslinking reaction was at most 15 mol % by heat treatment for 20 min at 200° C. Applying partially neutralized PAA (DN=10 mol %) raised the degree to about 40 mol % under the same heat-treatment conditions. FTIR analysis revealed that the hydroxyl group of PVA in the film blended with unneutralized PAA was degraded to a greater degree than that with partially neutralized PAA as a result of heat treatment. It was found that heat treatment at a low pH condition enhances the degradation of the hydroxyl group of PVA, resulting in a decrease of the number of crosslinking sites by esterification.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

All publications, patents, and patent applications cited herein are hereby incorporated by reference in their entirety for all purposes.

41

Tables

Table 1 shows various illustrative IRM formulations discussed herein, in accordance with one or more embodiments of the invention.

Table 2 shows various crosslinkers used to crosslink PVA, in accordance with one or more embodiments of the invention.

Table 3 shows illustrative IRM formulations discussed herein, in accordance with one or more embodiments of the invention.

TABLE 1

| Formulation | PVA 5 g | Cross-linker | note | |
| --- | --- | --- | --- | --- |
| | PVA 5 g 5% solution | SSA (10% solution) | SSA | Sulfosuccinic acid |
| | | | SSA | Sulfosuccinic acid |
| 924k | 96 kd 88% DH SP$^2$ | 0.3 mL | SSA | Sulfosuccinic acid |
| 911J | 130 kd 88% DH | 0.3 mL | SSA | Sulfosuccinic acid |
| | | 0.3 mL | SSA | Sulfosuccinic acid |
| Cb | 67 kd 88% DH | 0.3 mL | SSA | Sulfosuccinic acid |
| Cf | 67 kd 88% DH | 0.4 mL | SSA | Sulfosuccinic acid |
| 101P | 61 kd DH99% Fluka | 0.3 mL | SSA | Sulfosuccinic acid |
| 101Q | 125 kd DH99% Sigma | 0.3 mL | SSA | Sulfosuccinic acid |
| M1 | R1130 | 0.3 mL | SSA | Sulfosuccinic acid |
| M2 | R1130 | 0.25 mL | SSA | Sulfosuccinic acid |
| M3 | R1130 | 0.2 mL | SSA | Sulfosuccinic acid |
| M4 | R1130 | 0.15 mL | SSA | Sulfosuccinic acid |
| M6 | R1130 | 0.6 mL | SSA | Sulfosuccinic acid |
| M8 | R1130 | 0.8 mL | SSA | Sulfosuccinic acid |
| 829A | 61 kd 98% DH | 0.4 mL | SSA | Sulfosuccinic acid |
| 829B | 47.1 kd 98%DH | 0.4 mL | SSA | Sulfosuccinic acid |
| 829C | 67 kd 88% DH | 0.4 mL | SSA | Sulfosuccinic acid |
| | | | SSA | Sulfosuccinic acid |

42

TABLE 1-continued

| Formulation | PVA 5 g | Cross-linker | note | |
| --- | --- | --- | --- | --- |
| NK1 | 67 kd 88% DH | 0.4mL | SSA | Sulfosuccinic acid |
| NK2 | 67 kd 88% DH | 0.6mL | SSA | Sulfosuccinic acid |
| NK3 | 67 kd 88% DH | 0.8 mL | SSA | Sulfosuccinic acid |
| | | PMA | | |
| E | R1130, 98% | 0.3 mL | PMA | Poly(methyl vinyl ether-alt-maleic acid) |
| F | 195 kd, 98% DH Fluka | 0.3 mL | PMA | Poly(methyl vinyl ether-alt-maleic acid) |
| 822B | 195 kd 98% DH | 0.3 mL | PMA | Poly(methyl vinyl ether-alt-maleic acid) |
| 822C | 125 kd 98% DH | 0.3 mL | PMA | Poly(methyl vinyl ether-alt-maleic acid) |
| | | Diazo sensitizer | | |
| G | R1130 | 1.2 g | CMI-18 (0.2 g/mL) | |
| H | R1130 | 0.9 g (diluted on instruction) | DiazoSensitizer from Murakami USA | |

TABLE 2

| Crosslinkers used on PVA. | |
| --- | --- |
| Freeze-thaw treatment | Malic acid |
| Heat treatment | Malonic acid |
| Acid-catalysed dehydration | Fumaric acid |
| γ-Irradiation | Poly(acrylic acid) |
| Persulphate treatment | Trimesic acid |
| Formaldehyde | Trimesoyl chloride |
| Glutaraldehyde | Toluene diisocyanate |
| Glyoxal | Glycidyl acrylate |
| Terephthaldehyde | Divinyl sulphone |
| Acrolein & methacrolein | Boric acid |
| Urea formaldehyde/$H_2SO_4$ | 1,2-Dibromoethane |
| Citric acid | Tetraethoxysilane |
| Maleic acid & anhydride | γ-Glycidoxypropyltrimethoxysilane |
| Maleic anhydride copolymers with vinyl methyl ether | γ-Mercaptopropyltrimethoxysilane |

TABLE 3

| Formulation | E | F | 822C(9) | 822D | 19 | 14 |
| --- | --- | --- | --- | --- | --- | --- |
| PVA(5%), DH | R1130, 98% | Fluka195 kd, 98% | 125 kd 98% DH | 205 kd 88% DH | R1130, 98% | 195 kd sigma, DH98% |
| Cross-linker | PMA 0.3 mL | PMA 0.3 mL | PMA 0.3 mL | PMA 0.3 mL | PMA 0.4 mL | PMA 0.5 mL |
| Heating condition | 140-150° C. | 140-150° C. | 140-150° C. | 140-150° C. | | |
| | PMA | Poly(methyl vinyl ether-alt-maleic acid) | | | | |
| | SSA | Sulfosuccinic acid | | | | |
| | 12% crosslinker based on polymer | | | | | |

TABLE 3-continued

| Formulation | E | F | 822C(9) | 822D | 19 | 14 |
|---|---|---|---|---|---|---|
| (PVA) by weight DH, degree of hydrolysis | | | | | | |

The invention claimed is:

1. A method of making a sensor apparatus for implantation within a mammal comprising the steps of:

providing a base layer;

forming a conductive layer on the base layer, wherein the conductive layer includes a working electrode;

forming an interference rejection membrane over the working electrode, wherein the interference rejection membrane is selected to inhibit the diffusion of ascorbic acid, uric acid and/or acetaminophen therethrough and comprises poly(vinyl alcohol) polymers crosslinked with sulfosuccinic acid or poly(methyl vinyl ether-alt-maleic acid);

forming an analyte sensing layer over the interference rejection membrane, wherein the analyte sensing layer includes an oxidoreductase; and forming an analyte modulating layer over the analyte sensing layer, wherein the analyte modulating layer includes a composition that modulates the diffusion of the analyte therethrough.

2. The method of claim 1, wherein:

the interference rejection membrane comprises 5 wt % poly(vinyl alcohol) crosslinked with 10-20 wt % crosslinker.

3. The method of claim 1, wherein materials forming the interference rejection membrane and materials forming the analyte modulating layer are selected so that the diffusivity of $O_2$ diffusion coefficient through said layers is at least $1.0 \times 10^{-5}$ cm2/s.

4. The analyte sensor apparatus of claim 1, wherein the poly(vinyl alcohol) polymer has a molecular weight (Mw) of at least 45K.

5. The method of claim 1, wherein the degree of hydrolysis of the poly(vinyl alcohol) polymer is from 87% to 98%.

6. The method of claim 1, wherein the interference rejection membrane is between 0.3-2 μm thick, and formed on the electrode by a spin coating process at 400-1200 rpm and cured at a temperature between 130° C.-150° C.

7. The method of claim 1, wherein the interference rejection membrane is between 0.4-0.8 μm thick, and formed on the electrode by a spin coating process at 400-500 rpm and cured at a temperature of 130° C. for at least 40 minutes.

8. A method of making a sensor apparatus for implantation within a mammal comprising the steps of:

providing a base layer;

forming a conductive layer on the base layer, wherein the conductive layer includes a working electrode;

forming an interference rejection membrane over the working electrode, wherein the interference rejection membrane is selected to inhibit the diffusion of ascorbic acid, uric acid and/or acetaminophen therethrough and comprises poly(vinyl alcohol) polymers crosslinked with a crosslinking agent selected from the group consisting of sulfosuccinic acid (SSA), maleic acid, citric acid, oxalic acid, fumaric acid, poly(acrylic acid), poly(acrylic acid-co-maleic acid) (PAM), succinic acid, malonic acid, and poly(methyl vinyl ether-alt-maleic acid) and the interference rejection membrane is crosslinked with 5-35 wt % crosslinking agent;

forming an analyte sensing layer over the interference rejection membrane, wherein the analyte sensing layer includes an oxidoreductase; and forming an analyte modulating layer over the analyte sensing layer, wherein the analyte modulating layer includes a composition that modulates the diffusion of the analyte therethrough.

9. The method of claim 8, wherein the interference rejection membrane comprises 5 wt % poly(vinyl alcohol) crosslinked with 10-20 wt % of the crosslinking agent.

10. The method of claim 8, wherein the poly(vinyl alcohol) polymer has a molecular weight (Mw) of at least 45K.

11. The method of claim 8, wherein the interference rejection membrane inhibits the diffusion therethrough of compounds having a molecular weight greater than 140 Daltons.

12. The method of claim 11, wherein the interference rejection membrane inhibits the diffusion of acetaminophen therethrough in a manner that decreases a signal in the analyte sensor apparatus that results from a concentration of acetaminophen by at least 50% as compared to a control analyte sensor apparatus lacking the interference rejection membrane.

13. The method of claim 12, wherein the crosslinking agent is sulfosuccinic acid.

14. The method of claim 13, wherein the interference rejection membrane comprises 5-35 wt % sulfosuccinic acid.

15. The method of claim 11, wherein the interference rejection membrane comprises 5 wt % poly(vinyl alcohol) crosslinked with 10 wt % sulfosuccinic acid.

16. The method of claim 8, wherein the degree of hydrolysis of the poly(vinyl alcohol) polymer is from 87% to 98%.

17. The method of claim 8, wherein the interference rejection membrane has a thickness of 0.3-2 μm.

18. The method of claim 17, wherein the interference rejection membrane has a thickness of 0.4-0.8 μm.

* * * * *